(12) United States Patent
Kuroiwa et al.

(10) Patent No.: US 7,563,893 B2
(45) Date of Patent: Jul. 21, 2009

(54) 3-PHENYL-CINNOLINE ANALOGUE AND ANTITUMOR AGENT USING THE SAME

(75) Inventors: Shunsuke Kuroiwa, Kumagawa (JP); Junko Odanaka, Tokyo (JP); Sakiko Maruyama, Tokyo (JP); Yoshitaka Sato, Yoshikawa (JP); Arihiro Tomura, Tokyo (JP); Hiroshi Sato, Saitama (JP); Yoshikazu Suzuki, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 364 days.

(21) Appl. No.: 10/538,126

(22) PCT Filed: Dec. 10, 2003

(86) PCT No.: PCT/JP03/15767

§ 371 (c)(1),
(2), (4) Date: Jun. 6, 2005

(87) PCT Pub. No.: WO2004/052866

PCT Pub. Date: Jun. 24, 2004

(65) Prior Publication Data

US 2006/0058305 A1    Mar. 16, 2006

(30) Foreign Application Priority Data

Dec. 10, 2002 (JP) .............................. 2002-357556
Jun. 11, 2003 (JP) .............................. 2003-166082
Jun. 27, 2003 (JP) .............................. 2003-183766

(51) Int. Cl.
*C07D 237/28* (2006.01)
*C07D 471/04* (2006.01)
*A61P 35/00* (2006.01)
*A61K 31/498* (2006.01)
*C07D 213/69* (2006.01)

(52) U.S. Cl. ....................... 544/235; 546/296; 544/236

(58) Field of Classification Search ................. 514/248; 540/461, 578; 544/235, 236
See application file for complete search history.

(56) References Cited

U.S. PATENT DOCUMENTS 5,919,808 A * 7/1999 Petrie et al. ................. 514/372
6,008,208 A * 12/1999 Petrie et al. ................. 514/150
6,121,266 A 9/2000 Dolle et al. ............ 514/252.03

OTHER PUBLICATIONS

Journal of Medicinal Chemistry, 1976, vol. 19, No. 4, pp. 508-511; "Central Nervous System Active 5-Oxo-1,4,5,6,7,8-hexahydrocinnolines"; Kuppuswamy Nagarajan et al.

J.Med.Chem. 1997, 40, 4290-4301; F.George Njoroge et al.; "Structure-Activity Relationship of 3-Substituted N-(Pyridinylacetyl)-4-(8-chloro-5,6-dihydro-11H-benzo[5,6]cyclohepta[1,2-b]pyridine-11-ylidene)-piperidine Inhibitors of Farnesyl-Protein Transferase: Design and Synthesis of in Vivo Active Antitumor Compounds".
Indian Journal of Chemistry, vol. 25B, Jul. 1986, pp. 697-708; K.Nagarajan et al.; "Synthesis & Reactions of 4,6,7,8-Tetrahydro-5(1H)-cinnolinones".
J.Med.Chem. 1998, 41, 3812-3820; Cosimo Altomare, et al.; "Inhibition of Monoamine Oxidase-B by Condensed Pyridazines and Pyrimidines: Effects of Lipophilicity and Structure-Activity Relationships".
The International Search Report dated Jan. 27, 2004.
European communication dated Sep. 11, 2008.
Database Caplus—Chemical Abstracts Service, Ramadas, Sukuru Raghu et al.; "Condensed nitrogen heterocycles derviced from indian-1, 3-dione"—XP002441182, 1984.
Journal of Medicinal Chemistry, 1976, vol. 19, No. 4; Kuppuswamy Nagarajan et al.; "Central Nervous System Active 5-Oxo-1,4,5,6,7,8-hexahydrocinnolines"; pp. 508-511.
European communication dated Jul. 19, 2007.

* cited by examiner

*Primary Examiner*—Mark L Berch
*Assistant Examiner*—Cecilia M Jaisle
(74) *Attorney, Agent, or Firm*—Nields, Lemack & Frame, LLC

(57) ABSTRACT

The present invention relates to a 3-phenyl-cinnoline compound or a physiologically acceptable salt thereof, and a cell proliferation inhibitor and an antitumor agent comprising the same, as an active ingredient. The cinnoline compounds have the following general formula (1) or (2):

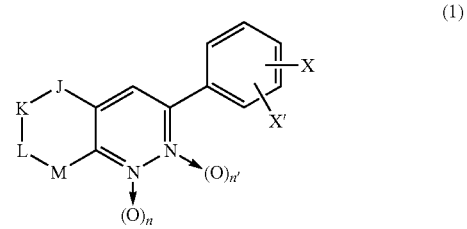

(1)

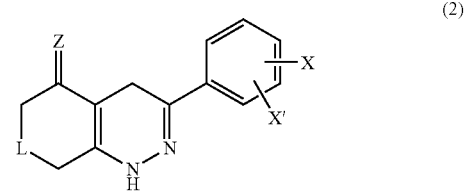

(2)

1 Claim, No Drawings

3-PHENYL-CINNOLINE ANALOGUE AND ANTITUMOR AGENT USING THE SAME

BACKGROUND OF THE INVENTION

1. Technical Field

The present invention relates to a 3-phenyl-cinnoline analogue or a physiologically acceptable salt thereof, and an antitumor agent comprising the same as an active ingredient.

2. Prior Art

Malignant tumor is a cell group which continues to proliferate in vivo deviated from normal biological mechanism and causes death of a host unless proper treatment is given. Treatment of malignant tumor is generally surgical excision, radiation irradiation, hormonotherapy or chemotherapy, and especially surgical operation is the first choice for treatment of malignant solid tumor. Radiotherapy, hormonotherapy and chemotherapy are generally used for preoperative or postoperative supplemental therapy or for treatment of malignant solid tumor which was judged impossible to treat surgically. Hormonotherapy and chemotherapy are used for narrowing area of surgical excision, or for degenerating and disappearing tumor, which can not be excisable completely by surgical operation, and preventing recurrence. However, at present, these operations cause patients with cancer physical and mental pains, and further when tumor metastasizes, excision area has to be broadened, and more difficult operational technique is required. Reason why chemotherapy is not major therapeutic means is that such an antitumor agent has not been developed as does not causes serious adverse effects and exhibits clinical effectiveness. Consequently, an antitumor agent having excellent antitumor effect against malignant solid tumor has been required.

In the non-patent document 1 hereinbelow, cinnoline derivatives acting on a central nervous system, and in the non-patent document 2, cinnoline derivatives having monoamine oxidase inhibitory action are reported. However, there are neither descriptions on a cinnoline analogue represented by the following general formula (1) of the present invention nor descriptions on antitumor activities of a cinnoline analogue.

In the following non-patent document '3, synthesis and reaction of cinnoline derivatives are described, however there is no description on antitumor actions of a cinnoline analogue.

REFERENCES

[Non-Patent Document 1]
Rashmi K. Shah et al., Central Nervous System Active 5-Oxo-1,4,5,6,7,8-Hexahydrocinnolines, Journal of Medicinal Chemistry, 1976, vol. 19, p. 508-511

(Non-Patent Literature 2)
Angelo Carotti et al., Inhibition of Monoamine Oxidase-B by Condensed Pyridazines and Pyrimidines: Effects of Lipophilicity and Structure-Activity Relationships, Journal of Medicinal Chemistry, 1998, vol. 41, p. 3812-3820

(Non-Patent Literature 3)
K. Nagarajan et al., Synthesis & Reactions of 4,6,7,8-Tetrahydro-5(1H)-cinnolinones, Indian Journal of Chemistry, 1986, vol. 25B, p. 697-708

DISCLOSURE OF THE INVENTION

Inventors of the present invention have found that a 3-phenyl-cinnoline analogue or a pharmaceutically acceptable salt thereof has cell proliferation inhibitory action and antitumor activity and have thus completed the present invention.

The present invention relates to 1)-14) aspects below.

1. An antitumor agent comprising a 3-phenyl-cinnoline analogue represented by the following general formula (1) or (2):

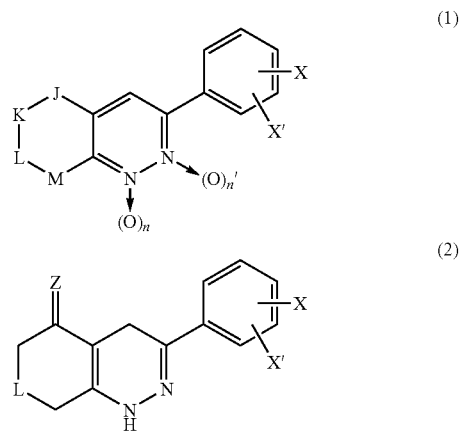

wherein J is A-C-B (C is a carbon atom); A is an O—Y group (O is an oxygen atom; Y is a hydrogen atom, a lower alkyl group which may be substituted by a phenyl group, a lower acyl group or an amino acid residue which may be protected); B is a hydrogen atom, a lower alkyl group, or a carbonyl group or a substituted imino group together with A; K is $(CH_2)_q$; L is N—W (N is a nitrogen atom) or W—C—W' (C is a carbon atom); W and W' each independently is a lower alkyl group which may have a substituent selected from a group consisting of a hydroxyl group, a lower alkoxyl group and a phenyl group, a phenyl group, a carboxyl group, a lower alkoxycarbonyl group or a hydrogen atom; M is $(CH_2)_m$, or J-K-L-M is C(O—Y)=CH—C(W)=CH (Y and W have the same meanings hereinabove); Z is an oxygen atom or N-Q (Q is an amino group, a lower alkylamino group, a hydroxyl group or a lower alkoxyl group); X and X' each independently is a lower alkyl group, a lower alkoxycarbonyl group, a lower acylamino group, a lower alkoxyl group, a halogenated lower alkyl group, a nitro group, a cyano group, a halogen atom or a hydrogen atom; m and q each independently is an integer of 0 to 3; and n and n' each independently is 0 or 1, or a physiologically acceptable salt thereof as an active ingredient.

2. The antitumor agent according to the above-described 1 wherein the 3-phenyl-cinnoline analogue is a compound represented by the following general formula (3):

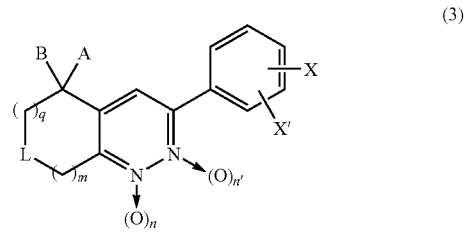

wherein A is O—Y group (Y is a hydrogen atom, a lower alkyl group which may be substituted by a phenyl group, a lower acyl group or an amino acid residue which may be protected);

B is a hydrogen atom, a lower alkyl group, or a carbonyl group or a substituted imino group together with A; L is N—W or W—C—W'; W and W' each independently is a lower alkyl group which may have a substituent selected from a group consisting of a hydroxyl group, a lower alkoxyl group and a phenyl group, a phenyl group, a carboxyl group, a lower alkoxycarbonyl group or a hydrogen atom; X is a lower alkyl group, a lower alkoxycarbonyl group, a lower acylamino group, a lower alkoxyl group, a trifluoromethyl group, a nitro group, a cyano group or a halogen atom; X' is a lower alkyl group, a lower alkoxycarbonyl group, a lower acylamino group, a lower alkoxyl group, a trifluoromethyl group, a nitro group, a cyano group, a halogen atom or a hydrogen atom; m and q each independently is an integer of 0 to 3; and n and n' each independently is 0 or 1.

3. The antitumor agent according to the above-described 2, wherein B is a hydrogen atom; L is W—C—W'; W and W' each independently is a lower alkyl group which may have a substituent selected from a group consisting of a hydroxyl group, a lower alkoxyl group and a phenyl group, or a hydrogen atom; X is a 3-trifluoromethyl group, a 3-nitro group, a 3-cyano group or a 3-bromo group; X' is a hydrogen atom; m and q each individually is 1; n is 0 or 1; and n' is 0.

4. The antitumor agent according to the above-described 3, wherein W and W' each independently is a hydrogen atom or a lower alkyl group, and X is a 3-trifluoromethyl group.

5. The antitumor agent according to the above-described 2, wherein Y is a glycyl group, an alanyl group, a valyl group or an α-glutamyl group; B is a hydrogen atom; L is H—C—CH₃; X is a 3-trifluoromethyl group; X' is a hydrogen atom; m and q each individually is 1; n is 0 or 1; and n' is 0.

6. The antitumor agent according to the above-described 1, wherein the 3-phenyl-cinnoline analogue is a compound represented by the following general formula (4):

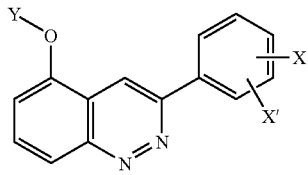

(4)

wherein X and X' each independently is a lower alkyl group, a lower alkoxycarbonyl group, a lower acylamino group, a lower alkoxyl group, a trifluoromethyl group, a nitro group, a cyano group, a halogen atom or a hydrogen atom; Y is a lower alkyl group which may be substituted by a phenyl group, a lower acyl group or a hydrogen atom; and W is a lower alkyl group which may have a substituent selected from a group consisting of a hydroxyl group, a lower alkoxyl group and a phenyl group, a phenyl group, a carboxyl group, a lower alkoxycarbonyl group or a hydrogen atom.

7. The antitumor agent according to the above-described 6, wherein X is a trifluoromethyl group, a nitro group, a cyano group or a halogen atom; X' is a hydrogen atom; and W is a lower alkyl group which may have a substituent selected from a group consisting of a hydroxyl group, a lower alkoxyl group and a phenyl group.

8. The antitumor agent according to the above-described 7, wherein X is a 3-trifluoromethyl group, a 3-nitro group, a 3-cyano group or a 3-halogen atom; and W is a non-substituted lower alkyl group.

9. The antitumor agent according to the above-described 1, wherein a 3-phenyl-cinnoline analogue is a compound represented by the following general formula (5):

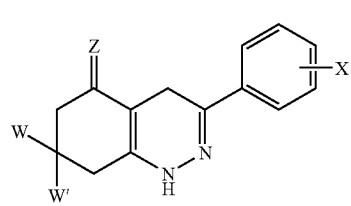

(5)

wherein W and W' each independently is a hydrogen atom or a lower alkyl group; X is a halogenated lower alkyl group; Z is an oxygen atom or N-Q; Q is an amino group, a lower alkylamino group, a hydroxyl group or a lower alkoxyl group.

10. The antitumor agent according to the above-described 9, wherein W is a hydrogen atom or a methyl group; W' is a hydrogen atom or a methyl group; X is a 3-trifluoromethyl group; and Z is an oxygen atom.

11. The antitumor agent according to the above-described 9, wherein W is a hydrogen atom or a methyl group; W' is a hydrogen atom or a methyl group; X is a 3-trifluoromethyl group; and Z is N—NH₂.

12. The antitumor agent according to the above-described 1, wherein the 3-phenylcinnoline analogue is 7-methyl-3-(3-trifluoromethyl)-7,8-dihydro-6H-cinnolin-5-one, 7-methyl-3-(3-trifluoromethyl)-5,6,7,8-tetrahydrocinnolin-5-ol, 7-methyl-3-(3-trifluoromethylphenyl)cinnolin-5-ol, 7-methyl-1-oxy-3-(3-trifluoromethyl)-5,6,7,8-tetrahydrocinnolin-5-ol, 5-glycyloxy-7-methyl-3-(3-trifluoromethyl)-5,6,7,8-tetrahydrocinnoline, 5-(L-alanyl)oxy-7-methyl-3-(3-trifluoromethyl)-5,6,7,8-tetrahydrocinnoline, 5-(L-valyl)oxy-7-methyl-3-(3-trifluoromethyl)-5,6,7,8-tetrahydrocinnoline, 5-(L-α-glutamyl)oxy-7-methyl-3-(3-trifluoromethyl)-5,6,7,8-tetrahydrocinnoline.

13. A cell proliferation inhibitor comprising the 3-phenyl-cinnoline analogue according to any one of the above-described 1-12 or the physiologically acceptable salt thereof as an active ingredient.

14. The 3-phenyl-cinnoline analogue according to any one of the above-described 1-12 or the physiologically acceptable salt thereof, proviso that a compound wherein Z is an oxygen atom is excluded.

BEST MODE FOR CARRYING OUT THE INVENTION

An antitumor agent of the present invention contains a 3-phenyl-cinnoline analogue represented by the above general formula (1) or (2) or a physiologically acceptable salt thereof as an active ingredient.

A "lower alkyl group" in a substituent of the general formula (1) or (2) means, if not otherwise defined, a straight chain or branched chain alkyl group having 1 to 6 carbon atoms, for example, a methyl group, an ethyl group, a n-propyl group, an isopropyl group, a n-butyl group, a sec-butyl group, a tert-butyl group, a n-pentyl group, an isopentyl group, a neopentyl group, a n-hexyl group, etc., a preferable group includes a methyl group, an ethyl group and an isopropyl group, and particularly preferable group is a methyl group.

A "lower acyl group" in a substituent of the general formula (1) or (2) means a non-substituted straight chain or branched chain acyl group having 1 to 6 carbon atoms, for example, a formyl group, an acetyl group, a propionyl group, a n-butyryl group, an isobutyryl group, a valeryl group, an isovaleryl group, a pivaloyl group, a hexanoyl group, etc., a preferable group is an acetyl group.

Further, in a substituent of the general formula (1), an "optionally protected amino acid residue" includes an α-amino acid residue generally known as an essential amino acid, in which the side chain and/or N terminal may be protected, proviso that absolute conformation may be L or D. A bond with an oxygen atom is preferably an ester bond with a carboxylic acid group at the main chain or side chain. An example of a protected functional group includes an amino group, a carboxyl group, a guanidino group, a hydroxyl group, a thiol group, etc. A protective group is not especially limited and such one as used in common peptide synthesis reaction, etc. can be included. An example of a representative protective group includes specifically alkoxycarbonyl groups such as a tert-butoxycarbonyl group and a benzyloxycarbonyl group; alkyl groups such as a methyl group, a tert-butyl group and a benzyl group; and acyl groups such as an acetyl group and a benzoyl group. That is amino acid residues which may be protected include an N-(tert-butoxycarbonyl)-L-valyl group, an O-benzyl-D-tyrosyl group, an N-(tert-butoxycarbonyl)-L-prolyl group, an N-(tert-butoxycarbonyl)-L-phenylalanyl group, a L-alanyl group, a L-valyl group, a L-α-glutamyl group, a glycyl group, etc. The preferable groups include a L-alanyl group, a L-valyl group, a L-α-glutamyl group, a glycyl group, etc.

An example of a lower alkyl group substituted with a phenyl group in a substituent of the general formula (1) includes specifically, a benzyl group, a 1-phenylethyl group, a 2-phenylethyl group, a benzyl group, etc., and a benzyl group, etc., is preferable.

In a substituent of the general formula (1) or (2), a "lower alkoxyl group" means a straight chain or branched chain alkoxyl group having 1 to 6 carbon atoms, for example, a methoxy group, an ethoxy group, a n-propoxy group, an isopropoxy group, a n-butoxy group, an isobutoxy group, a tert-butoxy group, a n-pentyloxy group, an isopentyloxy group, a n-hexyloxy group, etc., and a methoxy group and an ethoxy group are preferable groups among them.

In a substituent of the general formula (1) or (2), "a lower alkyl group", having a substituent selected from a group consisting of a hydroxyl group, a lower alkoxyl group and a phenyl group, means a lower alkyl group having one or more same or different substituent, and includes specifically, a hydroxymethyl group, a 2-hydroxy-2-propyl group, a benzyl group, a methoxymethyl group, etc, and preferably a hydroxymethyl group and a benzyl group, etc.

In the general formula (1) or (2), "L is N (a nitrogen atom)-W" means an aliphatic heterocycle containing a nitrogen atom substituted with W. A specific example of L includes an N-methyl group, an N-benzyl group, an N-methoxymethy group, an N-(2-hydroxy)methyl group, etc., and preferably an N-benzyl group and an N-methyl group.

In the general formula (1) or (2), "L is W—C (a carbon atom)-W'" means an aliphatic carbon ring substituted with W and W'. A specific example of W and W' is that W is a hydrogen atom and W' is a methyl group, an ethyl group, an isopropyl group, an ethoxycarbonyl group, a carboxyl group, a hydroxymethyl group, a 2-hydroxy-2-propyl group, a phenyl group or a hydrogen atom, etc., or W and W' are both methyl groups, etc. Preferably, W is a hydrogen atom and W' is a methyl group or an isopropyl group.

In the general formula (1) or (2), a "lower alkoxycarbonyl group" means a group wherein the above lower alkoxyl group is bound with a carbonyl group, and includes specifically, a methoxycarbonyl group, an ethoxycaybonyl group and n-propyloxycarbonyl group, and preferably a methoxycarbonyl group and an ethoxycarbonyl group.

In the general formula (1) or (2), a "lower alkylamino group" means a group wherein one or two of the above lower alkyl groups is bound to a nitrogen atom, and includes specifically, a methylamino group, a dimethylamino group, an ethylamino group, a diethylamino group, a n-propylamino group and a di(n-propyl)amino group, etc.

In the general formula (1), J represents "A-C (a carbon atom)-B", wherein A and B may form a carbonyl group (C=O) or a substituted imino group (C=N— (a substituent)). An example of a substituent in a substituted imino group is an amino group, a lower alkylamino group, a hydroxyl group or a lower alkoxyl group, etc.

In the general formula (1) or (2), an example of a "halogen atom" is a fluorine atom, a chlorine atom, a bromine atom or an iodine atom, and is preferably a bromine atom or a fluorine atom.

In the general formula (1) or (2), a "lower acylamino group" includes an amino group bound with the above lower acyl group, and specifically, for example, a formylamino group, an acetylamino group, a propanoylamino group, etc., and preferably an acetylamino group.

In the general formula (1) or (2), a lower alkyl group in a "halogenated lower alkyl group" is the same group as the above lower alkyl group, and a preferable group is also the same as above. A halogen atom in a "halogenated lower alkyl group" includes similar one as above, i.e. a fluorine atom, a chlorine atom, a bromine atom or an iodine atom. Substitution number of halogen atoms which are included in the present invention is from one to the maximum substitutable number, and in case of plural substitutions, substituting halogen atoms can be the same or different. Specifically, a 1-chloropropyl group, a trichloromethyl group, a trifluoromethyl group, a 1,1,1-trifluoroethyl group, a pentafluoroethyl group and a 1,1-difluoro-1-chloroethyl group are included, and preferably a pentafluoroethyl group, a trifluoromethyl group, etc., and particularly preferably a trifluoromethyl group.

"J-K-L-M is C(O—Y)=CH—C(W)=CH (Y and W indicate the same meanings as above)" means cinnoline skeleton structure, in which a benzene ring condensed with a pyridazine ring. Specifically, for example, it is a compound represented by the above general formula (4).

In the general formula (1) or (2), X and X' are positioned on a benzene ring as substituents, and positions thereof are not specifically limited. Consequently, all isomers thereof are included within the scope of the present invention, and a mono-substituent at position-3 is preferable. A preferable substituent includes a trifluoromethyl group, a nitro group, a cyano group, a bromine atom, and a 3-trifluoromethyl group is especially preferable.

In the general formula (1) of the present invention, each of m and q is independently an integer of 0 to 3, to provide a 4-10 membered ring, forming a condensed ring with a pyridazine ring, preferably a 5-7 membered ring, more preferably a 6 membered ring, in which both m and q represent 1.

In the general formula (1) of the present invention, "n, n' is 1" means N-oxide, and preferably both n and n' are 0, or any one of n and n' is 1.

As an active ingredient, a 3-phenyl-cinnoline analogue, of an antitumor agent of the present invention, a compound represented by the general formula (3) hereinbefore is also included. In a compound of the general formula (3), a lower alkyl group which may be substituted with a phenyl group, a lower acyl group, an amino acid residue which may be protected, a lower alkyl group, a lower alkoxy group, a phenyl group, a lower alkoxycarbonyl group, a lower acylamino group, a halogen atom and a substituted imino group have the same meaning as each substituent in the general formula (1), and preferable groups are also the same as mentioned hereinbefore. Further, m, q, n and n' are the same as each m, q, n and n' in the general formula (1), and preferable range is also the same.

In the most preferable compound of the general formula (3), B is a hydrogen atom; L is W—C—W'; W and W' each independently is a lower alkyl group, which may optionally have a substitution group selected from a group consisting of a hydroxyl group, a lower alkoxyl group and a phenyl group, or a hydrogen atom; X is a 3-trifluoromethyl group, a 3-nitro group, a 3-cyano group or a 3-bromo group; X' is a hydrogen atom; m and q are both 1; n is 0 or 1; and n' is 0. In a more preferable compound, W and W' each independently is a hydrogen atom or a lower alkyl group; and X is a 3-trifluoromethyl group. Also in a preferable compound, Y is a glycyl group, an alanyl group, a valyl group or an α-glutamyl group; and B is a hydrogen atom; L is H—C—CH$_3$; X is a 3-trifluoromethyl group; X' is a hydrogen atom; m and q are both 1; n is 0 or 1; and n' is 0.

An example of a compound of the general formula (3) includes such a compound as specifically shown in Table 1. In the Table, Ph represents a phenyl group, Et an ethyl group, Me a methyl group, Ac an acetyl group, Bn a benzyl group, Boc a tert-butoxycarbonyl group and t-Bu a tert-butyl group; mix means a mixture of syn form and anti form; and amino acids are expressed by commonly used abbreviations.

TABLE 1

| Comp No. | A, B | L | Isomer Type | q | m | n | n' | X | X' | optical |
|---|---|---|---|---|---|---|---|---|---|---|
| 1 | =O | C(H)Ph | — | 1 | 1 | 0 | 0 | 3-CF3 | H | (±) |
| 2 | =O | COOEt | — | 1 | 1 | 0 | 0 | 3-CF3 | H | (±) |
| 3 | —OH,H | COOEt | syn | 1 | 1 | 0 | 0 | 3-GF3 | H | (±) |
| 4 | —OH,H | COOH | syn | 1 | 1 | 0 | 0 | 3-CF3 | H | (±) |
| 5 | =O | COOH | — | 1 | 1 | 0 | 0 | 3-GF3 | H | (±) |
| 6 | —OH,H | C(H)Me | syn | 1 | 1 | 0 | 0 | 3-CF3 | H | (±) |
| 7 | —OH,H | C(H)Me | anti | 1 | 1 | 0 | 0 | 3-CF3 | H | (±) |
| 8 | —O-Pro(Boc),H | C(H)Me | anti syn | 1 1 | 1 1 | 0 0 | 0 0 | 3-CF3 3-CF3 | H H | (±) (+),(−) |
| 9 | —OH,H | C(H)Me | syn | 1 | 1 | 0 | 0 | 3-CF3 | H | (5R,7R) |
| 10 | —OH,H | C(H)Me | syn | 1 | 1 | 0 | 0 | 3-CF3 | H | (5S,7S) |
| 11 | —OAc,H | C(H)Me | syn | 1 | 1 | 0 | 0 | 3-CF3 | H | (±) |
| 12 | —OH,H | C(H)Me | syn | 1 | 1 | 1 | 0 | 3-CF3 | H | (±) |
| 13 | =O | C(H)Me | — | 1 | 1 | 1 | 0 | 3-CF3 | H | (±) |
| 14 | —OH,H | C(H)CH2OH | mix | 1 | 1 | 0 | 0 | 3-CF3 | H | (±) |
| 15 | =O | C(H)Me | — | 1 | 1 | 0 | 0 | 3-CN | H | (±) |
| 16 | —OH,H | C(H)Me | syn | 1 | 1 | 0 | 0 | 3-CN | H | (±) |
| 17 | —OH,H | C(Me)2 | — | 1 | 1 | 0 | 0 | 3-CF3 | H | (±) |
| 18 | —OH,H | CH2 | — | 1 | 1 | 0 | 0 | 3-CF3 | H | (±) |
| 19 | =O | C(H)Me | — | 1 | 1 | 0 | 0 | 3-Br | H | (±) |
| 20 | =O | C(H)Me | — | 1 | 1 | 0 | 0 | 3-N02 | H | (±) |
| 21 | =O | C(H)Me | — | 1 | 1 | 0 | 0 | 3-Me | H | (±) |
| 22 | =O | C(H)Me | — | 1 | 1 | 0 | 0 | 3C02Me | H | (±) |
| 23 | =O | C(H)Me | — | 1 | 1 | 0 | 0 | 3-NHAc | H | (±) |
| 24 | =O | C(H)Me | — | 1 | 1 | 0 | 0 | 3-F | H | (±) |
| 25 | =O | C(H)Me | — | 1 | 1 | 0 | 0 | 3-OMe | H | (±) |
| 26 | =O | NBn | — | 1 | 1 | 0 | 0 | 3-CF3 | H | — |
| 27 | =OH,Me | CHC(Me)2OH | mix | 1 | 1 | 0 | 0 | 3-CF3 | H | (±) |
| 28 | =O | C(H)Me | — | 1 | 1 | 0 | 0 | 3-F | 5-CF3 | (±) |
| 29 | —OH,H | C(H)Me | syn | 1 | 1 | 0 | 0 | 3-F | 5CF3 | (±) |
| 30 | —OH,Me | C(H)Me | mix | 1 | 1 | 0 | 0 | 3-CF3 | H | (±) |
| 31 | —O-Ala(Boc),H | C(H)Me | syn | 1 | 1 | 0 | 0 | 3-CF3 | H | single isomer |
| 32 | —O-Ala,H | C(H)Me | syn | 1 | 1 | 0 | 0 | 3-CF3 | H | single isomer |
| 33 | —O-Asp(a)(Boc)(6)(OtBu),H | C(H)Me | syn | 1 | 1 | 0 | 0 | 3-CF3 | H | single isomer |
| 34 | —O-Asp(a),H | C(H)Me | syn | 1 | 1 | 0 | 0 | 3-CF3 | H | single isomer |
| 35 | —O-Asp(B)(Boc)(a)(OtBu),H | C(H)Me | syn | 1 | 1 | 0 | 0 | 3-CF3 | H | single isomer |
| 36 | —O-Asp(B),H | C(H)Me | syn | 1 | 1 | 0 | 0 | 3-CF3 | H | single isomer |
| 37 | —O-Glu(a)(BOC)(y)(OtBu),H | C(H)Me | syn | 1 | 1 | 0 | 0 | 3-CF3 | H | single isomer |
| 38 | —O-Glu(a),H | C(H)Me | syn | 1 | 1 | 0 | 0 | 3-CF3 | H | single isomer |
| 39 | —O-Glu(y)(Boc)(a)(OtBu),H | C(H)Me | syn | 1 | 1 | 0 | 0 | 3-CF3 | H | single isomer |
| 40 | —O-Glu(y),H | C(H)Me | syn | 1 | 1 | 0 | 0 | 3-CF3 | H | single isomer |
| 41 | —O-Gly(Boc),H | C(H)Me | syn | 1 | 1 | 0 | 0 | 3-CF3 | H | single isomer |
| 42 | —O-Gly,H | C(H)Me | syn | 1 | 1 | 0 | 0 | 3-CF3 | H | single isomer |

TABLE 1-continued

| Comp No. | A, B | L | Isomer Type | q | m | n | n' | X | X' | optical |
|---|---|---|---|---|---|---|---|---|---|---|
| 43 | —O-Leu(Boc),H | C(H)Me | syn | 1 | 1 | 0 | 0 | 3-CF3 | H | single isomer |
| 44 | —O-Leu,H | C(H)Me | syn | 1 | 1 | 0 | 0 | 3-CF3 | H | single isomer |
| 45 | —O-Lys(Boc),H | C(H)Me | syn | 1 | 1 | 0 | 0 | 3-CF3 | H | single isomer |
| 46 | —O-Lys,H | C(H)Me | syn | 1 | 1 | 0 | 0 | 3-CF3 | H | single isomer |
| 47 | —O-Met(Boc),H | C(H)Me | syn | 1 | 1 | 0 | 0 | 3-CF3 | H | single isomer |
| 48 | —O-Met,H | C(H)Me | syn | 1 | 1 | 0 | 0 | 3-CF3 | H | single isomer |
| 49 | —O-Phe(Boc),H | C(H)Me | syn | 1 | 1 | 0 | 0 | 3-CF3 | H | single isomer |
| 50 | —O-Phe,H | C(H)Me | syn | 1 | 1 | 0 | 0 | 3-CF3 | H | single isomer |
| 51 | —O-Pro,H | C(H)Me | syn | 1 | 1 | 0 | 0 | 3-CF3 | H | single isomer |
| 52 | —O-Val(Boc),H | C(H)Me | syn | 1 | 1 | 0 | 0 | 3-CF3 | H | (5S,7S) |
| 53 | —O-Val,H | C(H)Me | syn | 1 | 1 | 0 | 0 | 3-CF3 | H | (5S,7S) |
| 54 | —OH,H | CH2 | — | 1 | 0 | 0 | 0 | 3-CF3 | H | (±) |
| 55 | —OH,H | CH2 | — | 0 | 1 | 0 | 0 | 3-CF3 | H | (±) |
| 56 | —OH,H | CH2 | — | 1 | 2 | 0 | 0 | 3-CF3 | H | (±) |
| 57 | —OH,H | CH2 | — | 2 | 1 | 0 | 0 | 3-CF3 | H | (±) |
| 58 | —OH,H | CH2 | — | 2 | 2 | 0 | 0 | 3-CF3 | H | (±) |
| 59 | OH,H | CH2 | — | 0 | 3 | 0 | 0 | 3-CF3 | H | (±) |
| 60 | —OH,H | C(H)Me | mix | 1 | 1 | 0 | 1 | 3-CF3 | H | (±) |
| 61 | —OH,H | CH2 | — | 1 | 1 | 0 | 0 | 3-CF3 | H | (±) |
| 62 | —OH,H | C(H)Me | syn | 1 | 1 | 0 | 0 | 3-CF3 | 5-CF3 | (±) |
| 63 | —OBn,H | C(H)Me | syn | 1 | 1 | 0 | 0 | 3-CF3 | H | (±) |
| 64 | =O | NPh | — | 1 | 1 | 0 | 0 | 3-CF3 | H | — |
| 65 | =O | NCO2Me | — | 1 | 1 | 0 | 0 | 3-CF3 | H | — |
| 66 | —OH,H | C(H)CH2OMe | mix | 1 | 1 | 0 | 0 | 3-CF3 | H | (±) |
| 67 | —O-(D)-Phe(Boc),H | C(H)Me | syn | 1 | 1 | 0 | 0 | 3-CF3 | H | (5S,7S) |
| 68 | —O-Val(Boc),H | C(H)Me | syn | 1 | 1 | 0 | 0 | 3-CF3 | H | (5R,7R) |
| 69 | —O-Val,H | C(H)Me | syn | 1 | 1 | 0 | 0 | 3-CF3 | H | (5R,7R) |
| 70 | —O-Val(Boc),H | C(H)Me | anti | 1 | 1 | 0 | 0 | 3-CF3 | H | (5S,7R) |
| 71 | —OH,H | C(H)Me | anti | 1 | 1 | 0 | 0 | 3-CF3 | H | (5S,7R) |
| 72 | —O-Val,H | C(H)Me | anti | 1 | 1 | 0 | 0 | 3-CF3 | H | (5S,7R) |
| 73 | —O-Val(Boc),H | C(H)Me | anti | 1 | 1 | 0 | 0 | 3-CF3 | H | (5R,7S) |
| 74 | —OH,H | C(H)Me | anti | 1 | 1 | 0 | 0 | 3-CF3 | H | (5R,7S) |
| 75 | —O-Val,H | C(H)Me | anti | 1 | 1 | 0 | 0 | 3-CF3 | H | (5R,7S) |
| 76 | =O | C(Me)2 | — | 1 | 1 | 0 | 0 | 3-CF3 | H | — |
| 77 | =O | CH2 | — | 1 | 1 | 0 | 0 | 3-CF3 | H | — |
| 78 | =O | C(H)Me | — | 1 | 1 | 0 | 0 | 3-CH2Cl | H | (±) |
| 79 | =O | C(H)Me | — | 1 | 1 | 0 | 0 | 3-CF3 | H | (±) |
| 80 | =O | C(H)Et | — | 1 | 1 | 0 | 0 | 2CH2Br | H | (±) |
| 81 | =O | C(H)Me | — | 1 | 1 | 0 | 0 | 4-C2F5 | H | (±) |
| 82 | =O | C(Me)2 | — | 1 | 1 | 0 | 0 | 3-CF3 | H | — |
| 83 | =N-NH2 | C(H)Me | — | 1 | 1 | 0 | 0 | 3-CF3 | H | (±) |
| 84 | =N-NHEt | C(H)iPr | — | 1 | 1 | 0 | 0 | 4-CH2Cl | H | (±) |
| 85 | =N—OMe | C(H)iPr | — | 1 | 1 | 0 | 0 | 2-CH2Cl | H | (±) |
| 86 | =N—OEt | C(Me)Et | — | 1 | 1 | 0 | 0 | 4-CF3 | H | (±) |
| 87 | —OH,H | C(H)Me | mix | 2 | 0 | 0 | 0 | 3-CF3 | H | (±) |
| 88 | =O | NMe | — | 1 | 1 | 0 | 0 | 3-CF3 | H | (±) |
| 89 | =O | NH | — | 1 | 1 | 0 | 0 | 3-CF3 | H | (±) |
| 90 | —OH,H | C(H)Me | mix | 1 | 1 | 1 | 1 | 3-CF3 | H | (±) |

An active ingredient, a 3-phenyl-cinnoline analogue, of an antitumor agent of the present invention includes also a compound represented by the above general formula (4). In a compound of the general formula (4), a lower alkyl group, a lower alkoxycarbonyl group, a lower acylamino group, a lower alkoxyl group, a trifluoromethyl group, a nitro group, a cyano group, a halogen atom, a lower alkyl group which may be subsitituted with a phenyl group, a lower acyl group, a phenyl group and a carboxyl group have the same meaning as each substituent in the general formula (1), and a preferable group also is the same as hereinbefore mentioned.

In a particularly preferable compound of the general formula (4), X is a trifluoromethyl group, a nitro group, a cyano group or a halogen atom; X' is a hydrogen atom; and W is a lower alkyl group which may have a substituent selected from a group consisting of a hydroxyl group, a lower alkoxyl group and a phenyl group. In a more preferable compound, X is a 3-trifluoromethyl group, a 3-nitro group, a 3-cyano group or a 3-halogen atom, and W is a non-substituted lower alkyl group.

An example of a compound of the general formula (4) includes specifically, 3-(3-trifluoromethylphenyl)cinnolin-5-ol, 7-methyl-3-(3-trifluoromethylphenyl)cinnolin-5-ol, 7-phenyl-3-(3-trifluoromethylphenyl)cinnolin-5-ol, 7-(2-methoxyethyl)-3-(3-trifluoromethylphenyl)cinnolin-5-ol, 7-ethoxycarbonyl-3-(3-trifluoromethylphenyl)cinnolin-5-ol, 3-(3-cyanophenyl)-7-methylcinnolin-5-ol, 3-(2-ethylphenyl)-7-methylcinnolin-5-ol, 3-(3-ethoxyphenyl)-7-methylcinnolin-5-ol, 3-(3-acetylaminophenyl)-5-acetyloxy-7-methylcinnoline, 5-methoxy-7-methyl-3-(3-trifluoromethylphenyl)cinnoline, 5-acetyloxy-7-methyl-3-(3-trifluoromethylphenyl)cinnoline, 5-benzyloxy-7-methyl-3-(3-trifluoromethylphenyl)cinnoline, 5-acetyloxy-7-methyl-3-(3-nitrophenyl)cinnoline, 3-(2-fluorophenyl)-7-isopropyl-5-methoxycinnoline, 3-(3,5-bis-trifluoromethylphenyl)-7-hydroxymethylcinnolin-5-ol, 7-benzyl-5-ethoxy-3-(2-methoxycarbonylphenyl)-cinnoline, 3-(3-acetylaminophenyl)cinnolin-5-ol, 3-(2-chloro-5-trifluoromethylphenyl)-5-hydroxycinnoline-7-carboxylic acid, and 3-(2-fluoro-5-trifluoromethylphenyl)-5-hydroxycinnoline-7-carboxylic acid, etc. and preferably 7-methyl-3-(3-trifluoromethylphenyl)cinnolin-5-ol, 5-methoxy-7-methyl-3-(3-trifluoromethylphenyl)cinnoline, 5-acetyloxy-7-methyl-3-(3-trifluoromethylphenyl)-cinnoline, and 5-benzyloxy-7-methyl-3-(3-trifluoromethylphenyl)cinnoline.

An active ingredient, a 3-phenyl-cinnoline analogue, of an antitumor agent of the present invention includes a compound represented by the above general formula (5). In a compound of the general formula (5), a lower alkyl group, a halogenated lower alkyl group, a lower alkylamino group and a lower alkoxyl group have the same meaning as each substituent in the general formula (1) or (2), and a preferable group is also the same as hereinbefore mentioned.

In a more preferable compound, W is a hydrogen atom or a methyl group; W' is a hydrogen atom or a methyl group; X is a 3-trifluoromethyl group; and Z is an oxygen atom or N—$NH_2$.

An example of a compound of the general formula (5) includes specifically, 7-methyl-3-(3-trifluoromethylphenyl)-4,6,7,8-tetrahydro-1H-cinnolin-5-one, 7,7-dimethyl-3-(3-trifluoromethylphenyl)-4,6,7,8-tetrahydro-1H-cinnolin-5-one, 7-methyl-3-(4-chloromethylphenyl)-4,6,7,8-tetrahydro-1H-cinnolin-5-one, and 3-(3-trifluoromethylphenyl)-4,6,7,8-tetrahydro-1H-cinnolin-5-one, etc.

A preferable example of a 3-phenyl-cinnoline analogue represented by the above general formula (1) includes specifically, 7-methyl-3-(3-trifluoromethyl)-7,8-dihydro-6H-cinnolin-5-one, 7-methyl-3-(3-trifluoromethyl)-5,6,7,8-tetrahydrocinnolin-5-ol, 7-methyl-3-(3-trifluoromethylphenyl)cinnolin-5-ol, 7-methyl-1-oxy-3-(3-trifluoromethyl)-5,6,7,8-tetrahydrocinnolin-5-ol, 5-glycyloxy-7-methyl-3-(3-trifluoromethyl)-5,6,7,8-tetrahydrocinnoline, 5-(L-alanyloxy)-7-methyl-3-(3-trifluoromethyl)-5,6,7,8-tetrahydrocinnoline, 5-(L-valyloxy)-7-methyl-3-(3-trifluoromethyl)-5,6,7,8-tetrahydrocinnoline, 5-(L-α-glutamyloxy)-7-methyl-3-(3-trifluoromethyl)-5,6,7,8-tetrahydrocinnoline, etc.

In a 3-phenyl-cinnoline analogue used in the present invention, when the compound has an asymmetric carbon and is present as an optically active compound or a racemate, such an optically active compound thereof, a mixture thereof and a racemate thereof are all included. Furthermore, a hydrate or a solvate thereof is also included.

In addition, a stereoisomer and a mixture thereof based on an imino bond (C=N) are all included within the above 3-phenyl-cinnoline analogue.

An example of a physiologically acceptable salt in the present invention includes salts of mineral acids such as hydrochloric acid, sulfuric acid, etc.; salts of organic acids such as acetic acid, succinic acid, fumaric acid, maleic acid, citric acid, benzoic acid, tartaric acid, methanesulfonic acid, p-toluenesulfonic acid, etc. A salt thereof can easily be prepared by a conventional salt-forming reaction.

As an antitumor agent of the present invention, included a 3-phenyl-cinnoline analogue, which can exhibit antitumor activity results from conversion by an oxidative reaction, reductive reaction, hydrolytic reaction, etc., by means of enzymatic action or gastric juice under physiological conditions in a body (e.g. physiological conditions described in "Development of Pharmaceuticals, Vol. 7, Molecular Design", Hirokawa Publishing Co., Tokyo, 1990, p. 163-198).

An antitumor agent of the present invention is administered orally or parenterally in a form of preparation such as suspension, emulsion, injection, inhalation, tablet, pill, granule, fine granule, powder, capsule, liquid preparation for oral use, suppository, liquid preparation for percutaneous use, patch for percutaneous use, ointment, liquid preparation for transmucosal use, patch for transmucosal use, etc., as a 3-phenyl-cinnoline analogue or a physiologically acceptable salt thereof, alone or as prepared by mixing with a excipient or a carrier. An additive such as a excipient or a carrier is selected from pharmaceutically acceptable substances, and a type and a composition thereof are determined by considering an administration route or a method for administration. For example, in case of injection, generally sodium chloride, saccharide such as glucose, mannitol, etc. are preferable. In case of oral preparation, starch, lactose, crystalline cellulose, magnesium stearate, etc., are preferable. If necessary, adjuvant such as an auxiliary, a stabilizing agent, a moistening agent or an emulsifier, a buffer and other conventionally used additives may optionally be contained in the above preparation.

Amount of the present compound in a preparation of the present invention varies depending on the preparation, however, is generally 0.1-100% by weight, preferably 1-98% by weight. For example, in case of injection, an active ingredient may be contained generally 0.1-30% by weight, preferably 1-10% by weight. In case of oral preparations, such forms as tablet, capsule, powder, granule, liquid preparation, dry syrup, etc. are used together with additives. A capsule, tablet, granule or powder contains generally 5-100% by weight, preferably 25-98% by weight of an active ingredient.

Dose level can be determined depending on age, sex, body weight, symptom and therapeutic objects, and therapeutic dose is generally 0.001-100 mg/kg/day for parenteral administration, while for oral administration, 0.01-500 mg/kg/day, preferably 0.1-100 mg/kg/day, is administered once or dividing into 2 to 4 times.

A 3-phenyl-cinnoline analogue used in the present invention can be produced by a method, for example, according to one described in the non-patent document 3 hereinbefore, and synthesis examples will be shown in the following Examples, however, a method is not especially limited to these Examples.

Specifically, for example, a compound, an α-halogenated substituted acetophenone derivative represented by the following general formula (6), can be purchased from Tokyo Kasei Kogyo Co. Ltd., etc., or can also be obtained by a method as follows: an acetophenone derivative, easily available commercially or obtainable by a production method in accordance with known reference, is easily halogenated by reaction at room temperature to a refluxing temperature, using N-halogenosuccinimide or a halogen alone such as bromine, iodine, etc., or a salt such as pyridinium bromide perbromide as a halogenation reagent, in a reaction solvent such as toluene, tetrahydrofuran, etc.

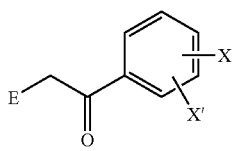

(6)

wherein E is a halogen atom; and X and X' have the same meanings hereinbefore.

As for 1,3-cycloalkanediones used for production of a compound, wherein L is W—C—W' in the above general formula (1), for example 1,3-pentanedione or 1,3-cycloheptannedione can be purchased from Sigma-Aldrich Co. Further, although a compound among 1,3-cyclohexanedione derivatives represented by the general formula (7) hereinbelow can be commercially available, it can also be prepared, if necessary, as illustrated in the scheme below: A mixture of a methyl vinyl ketone derivative (8) and a malonic ester derivative (9) is reacted at room temperature to a refluxing temperature in a solvent such as water, methanol, ethanol, etc. in the presence of a metal alkoxide such as sodium methoxide, sodium ethoxide, etc. or a hydroxide such as sodium hydroxide, potassium hydroxide, etc.:

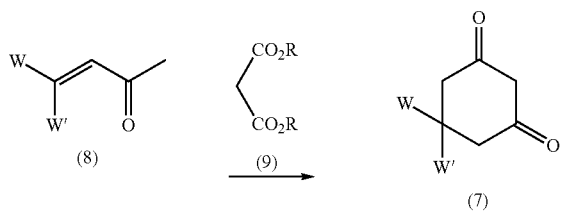

wherein R represents a lower alkyl group; and W and W' have the same meanings hereinabove.

Alternatively, as illustrated below, it can be prepared by hydrogenation of a resorcinol derivative (10) in the presence of a catalyst such as platinum, palladium, etc. in an organic solvent such as methanol, tetrahydrofuran, etc.;

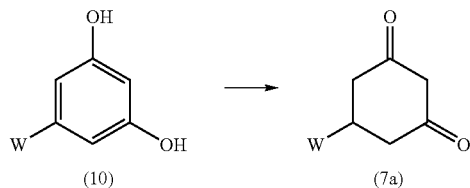

wherein W has the same meaning hereinabove.

A 5-aza-1,3-cyclohexanedione derivative (7b), which can be used for production of a compound of the general formula (1) wherein L is N—W, can be prepared in accordance with a method described in Archiv der Pharmazie, 1967, No. 300, p. 91-94. That is, an objective compound (7b) can be obtained as follows: A glycine derivative represented by the general formula (11) and bromoacetophenone are reacted at room temperature to a refluxing temperature in an organic solvent such as ethanol, dimethyl sulfoxide, tetrahydrofuran, etc. in the presence of a base such as sodium hydrogen carbonate, potassium carbonate, cesium carbonate, etc. to obtain a keto ester (12). The keto ester (12) is then reacted in an organic solvent such as ethanol, tert-butanol or dimethyl sulfoxide at 0° C. to room temperature in the presence of a base such as sodium methoxide, potassium tert-butoxide, sodium hydride, etc.

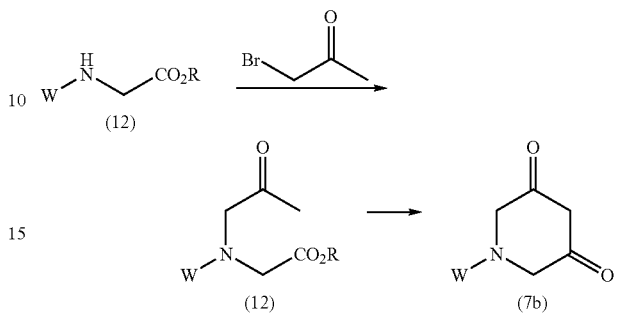

wherein R is a lower alkyl group and W has the same meaning hereinabove.

A 1,3-cyclohalkanedione derivative hereinabove and a compound of the above general formula (6) are reacted at room temperature to a refluxing temperature in an organic solvent such as dimethylsulfoxide, dichloromethane, chloroform, tetrahydrofuran, methanol, ethanol, etc. and in the presence of a base such as sodium hydride, sodium hydroxide, potassium hydroxide, potassium carbonate, cesium carbonate, sodium methoxide, sodium ethoxide, etc., to derivatize a compound represented by the general formula (13).

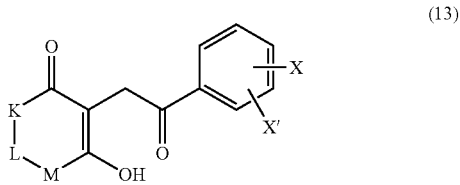

(13)

wherein K, L, M, X and X' have the same meanings hereinabove.

A compound represented by the general formula (13) is reacted with hydrazine hydrochloride in an organic solvent such as methanol, ethanol, etc. in the presence of a base such as triethylamine, pyridine, etc. at room temperature to a temperature of refluxing the organic solvent, to obtain a 4,6,7,8-hexahydro-1H-cinnolin-5-one derivative represented by the general formula (14).

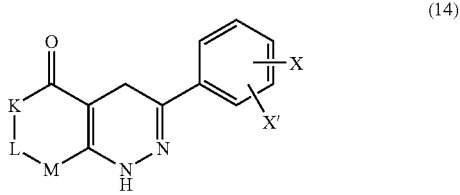

(14)

wherein K, L, M, X and X' have the same meanings hereinabove.

Further, a compound represented by the general formula (1a) hereinbelow can be obtained by air oxidation of said compound (14) by refluxing while heating in a basic solvent such as pyridine, triethylamine, etc., or by oxidation of the compound (14) by refluxing while heating in an organic solvent such as methanol, ethanol, tetrahydrofuran or mixed solvent thereof in the presence of metal catalyst such as palladium, platinum, etc., or by treating the compound (14) with an oxidizing agent such as cerium(IV) ammonium nitrate, 2,3-dichloro-5,6-dicyano-p-benzoquinone, etc.

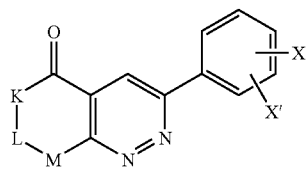

(1a)

wherein K, L, M, X and X' have the same meanings hereinabove.

Further, a compound represented by the general formula (1) wherein J is H—C—OH, and n and n' are 0 can be derivatized by reaction of a compound represented by the general formula (1a) with a reducing agent such as sodium borohydride, lithium aluminum hydride, lithium tri-tert-butoxyaluminum hydride, etc.; or an alkyl metal compound such as methyl lithium, isopropyl magnesium bromide, etc., in an organic solvent such as tetrahydrofuran, methanol, ethanol, etc., at ice-cooling temperature to room temperature.

Further, a compound of the general formula (1) with various Y groups can be produced by reaction of an acid chloride such as acetyl chloride, propanoyl bromide, etc. in an organic solvent such as dichloromethane, tetrahydrofuran, N,N-dimethyl formamide, ethyl acetate, etc., and in the presence or absence of an organic base such as pyridine, triethylamine, etc; or by reaction of a proteted amino acid such as N-tert-butoxycarbonyl-L-valine, N-benzyloxycarbonyl-D-proline or the like using a condensing agent such as dicyclohexylcarbodiimide, N-ethyl-N'-3-dimethylaminopropyl carbodiimide, etc. in the presence of dimethylaminopyridine; and by removing a protecting group for an amino acid in accordance with a conventional method such as the use of trifluoromethanesulfonic acid, hydrochloric acid, hydrogenolysis, etc.; or by reaction of an alkyl halide such as methyl iodide, benzyl bromide, etc. in an organic solvent such as N,N-dimethylformamide, dimethylsulfoxide, tetrahydrofuran, etc. in the presence of a base such as potassium tert-butoxide, sodium hydride and N,N-diisopropylethylamine.

Further, an N-oxide compound represented by the general formula (1) (n and/or n'=1) can be derivatized by reaction of an oxidizing agent such as m-chloroperbenzoic acid, peracetic acid, etc. with a compound of the general formula (1) wherein n and n' are 0, in an organic solvent such as methylene chloride, chloroform, etc.

A compound represented by the above general formula (4) can also be derivatized by reaction of a compound represented by the general formula (1a) (wherein any of W and W' is a hydrogen atom) with a halogenating agent such as cupric bromide, lithium chloride, iodine, etc. in the presence or absence of an organic solvent such as acetic acid, N,N-dimethylformamide, etc. at room temperature to a refluxing temperature, and if necessary, utilizing a base such as collidine, triethylamine, 1,8-diazabicyclo[5.4.0]-7-undecene, etc. Further, a compound represented by the general formula (4) hereinbefore can be derivatized by subjecting a compound represented by the general formula (1a) (wherein any of W and W' is a hydrogen atom) to direct oxidation reaction.

Further various derivatives can be produced by subjecting thus obtained compound to a conventional conversion reaction of a phenolic hydroxyl group. For example, various acyl groups can be introduced by reaction of an acid chloride such as acetyl chloride, propanoyl bromide, etc. in an organic solvent such as dichloromethane, tetrahydrofuran, N,N-dimethylformamide, ethyl acetate, etc. in the presence or absence of an organic base such as pyridine, triethylamine, etc., or various alkyl groups can be introduced by reaction of an alkyl halide such as methyl iodide, benzyl bromide, etc. in an organic solvent such as N,N-dimethylformamide, dimethylsulfoxide, tetrahydrofuran, etc. in the presence of a base such as potassium tert-butoxide, sodium hydride, N,N-diisopropylethylamine, etc.

Further, a derivative having an imino bond can also be obtained by heating at room temperature to a refluxing temperature a compound represented by the general formula (14) or (1a) with lower alkylhydrazines such as hydrazine hydrochloride, ethylhydrazine hydrochloride and methylhydrazine hydrochloride or lower alkyl hydroxylamines such as hydroxylamine hydrochloride, methoxylamine hydrochloride, O-ethyl hydroxylamine hydrochloride, etc. in an organic solvent such as methanol, ethanol, etc. in the presence of an organic base such as pyridine, triethylamine, etc., and, if necessary, by subjecting to oxidation reaction.

To isolate and purify an objective compound from a reaction mixture obtained by various methods for production hereinabove, conventional methods including solvent extraction, concentration, distillation, recrystallization, chromatography, etc. can be used, as appropriate.

The present invention includes a cell proliferation inhibitor comprising a 3-phenyl-cinnoline analogue represented by the above general formula (1), general formula (2), general formula (3), general formula (4) or general formula (5) or a physiologically acceptable salt thereof as an active ingredient. A compound similar to the above compound represented by the general formula (1), general formula (2), general formula (3), general formula (4) or general formula (5) can be used as a cell proliferation inhibitor, an antitumor agent, and a specific compound is also the same as above.

The present invention further includes a 3-phenyl-cinnoline analogue represented by the general formula (1) or (2) hereinbefore, excluding a compound wherein Z is an oxygen atom, or a physiologically acceptable salt thereof. Namely, the present invention includes a 3-phenyl-cinnoline analogue represented by the following general formula (1) or (2):

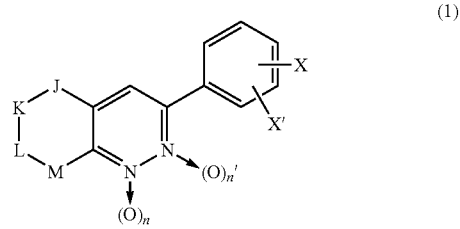

(1)

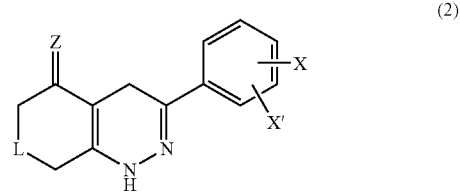

(2)

wherein J is A-C—B (C is a carbon atom); A is an O—Y group (O is an oxygen atom; Y is a hydrogen atom, a lower alkyl group which may optionally be substituted with a phenyl group, a lower acyl group or an amino acid residue which may be protected); B is a hydrogen atom, a lower alkyl group, or a carbonyl group or a substituted imino group together with A; K is $(CH_2)_q$; L is N—W (N is a nitrogen atom) or W—C—W' (C is a carbon atom); W and W' each independently is a lower alkyl group which may have a substituent selected from a group consisting of a hydroxyl group, a lower alkoxyl group and a phenyl group, a phenyl group, a carboxyl group, a lower alkoxycarbonyl group or a hydrogen atom; M is $(CH_2)_m$; or J-K-L-M is C(O—Y)=CH—C(W)=CH (Y and W have the same meanings hereinabove); Z is N-Q (Q is an amino group, a lower alkylamino group, a hydroxyl group or a lower alkoxyl group); X and X' each independently is a lower alkyl group, a lower alkoxycarbonyl group, a lower acylamino group, a lower alkoxyl group, a halogenated lower alkyl group, a nitro group, a cyano group, a halogen atom or a hydrogen atom; m and q each independently is an integer of 0 to 3; and n and n' each independently is 0 or 1, or a physiologically acceptable salt thereof.

Further, the present invention includes a 3-phenyl-cinnoline analogue represented by the general formula (3), general formula (4) or general formula (5), excluding a compound represented by the general formula (5) wherein Z is an oxygen atom, or a physiologically acceptable salt thereof.

Specifically, all of the compounds illustrated in the above general formulae (1) to (5), excluding a compound represented by the general formula (2) or the general formula (5) wherein Z is an oxygen atom, can be included.

EXAMPLES AND COMPARATIVE EXAMPLES

The present invention will be explained typically with Examples, Test Examples and Reference Examples, however, the present invention should not be limited thereto.

In the present invention, ESI is abbreviation of "Electron Spray Ionization" and FAB is abbreviation of "Fast Atom Bombardment", each of which is an ionization method in mass spectrometry for molecular weight measurement.

Hydrogen atom nuclear magnetic resonance spectra ($^1$H-NMR) is expressed by δ based on TMS (tetramethylsilane).

Example 1

Synthesis of 7-phenyl-3-(3-trifluoro-methylphenyl)-7,8-dihydro-6H-cinnolin-5-one A pyridine (5 ml) solution of 7-phenyl-3-(3-trifluoromethylphenyl)-4,6,7,8-tetrahydro-1H-cinnolin-5-one obtained in Reference Example 2 was stirred at 70° C. for 3 days. Residue obtained by concentration of the reaction liquid under reduced pressure was subjected to purification using silica gel column chromatography (hexane/ethyl acetate=3/1) to obtain a yellow crude product, which was further purified by suspension (hexane/ethyl acetate=3 ml/0.5 ml) to obtain an objective compound (124.0 mg, 48.9% in 2 steps).

$^1$H-NMR (200 MHzFT, TMS, CDCl$_3$) 2.93-3.23 (2H, complex), 3.51-3.75 (2H, complex), 3.76-3.97 (1H, m), 7.20-7.49 (5H, m), 7.70 (1H, t, J=7.8 Hz), 7.80 (1H, d, J=7.8 Hz), 8.31-8.42 (1H, m), 8.46 (1H, brs) MS(ESI) m/z 369 [M+H]$^+$

Example 2

Synthesis of ethyl 5-oxo-3-(3-trifluoro-methylphenyl)-7,8-dihydro-6H-cinnoline-7-carboxylate An objective compound was obtained by reaction similarly as in Reference Example 1 except that ethyl 3-hydroxy-5-oxo-cyclohex-3-ene carboxylate obtained in Reference Example 3 was used instead of 5-phenyl-1,3-cyclohexanedione, followed by processing similarly as in Reference Example 2 and Example 1.

$^1$H-NMR (200 MHzFT, TMS, CDCl$_3$) 1.26 (3H, dt, J=1.8, 7.1 Hz), 3.04 (2H, d, J=6.4 Hz), 3.62-3.87 (2H, m), 4.19 (1H, q, J=7.1 Hz), 7.69 (1H, t, J=7.7 Hz), 7.80 (1H, d, J=8.0 Hz), 8.31 (1H, s), 8.34 (1H, d, J=7.7 Hz), 8.44 (1H, s) MS(ESI) m/z 365 [M+H]$^+$

Example 3

Synthesis of ethyl 5-hydroxy-3-(3-trifluoro-methylphenyl)-5,6,7,8-tetrahydrocinnoline-7-carboxylate To an ethanol solution (0.5 mL) of 5-oxo-3-(3-trifluoromethylphenyl)-7,8-dihydro-6H-cinnoline-7-carboxylic acid ethyl ester (100 mg, 0.274 mmol) obtained in Example 2 was added sodium borohydride (10.4 mg, 0.274 mmol) and stirred at room temperature for 1 hour. After completion of reaction, the reaction liquid was quenched with a 1N aqueous solution of potassium hydrogen sulfate (1 mL) and extracted with ethyl acetate (3 ml), followed by drying with sodium sulfate, filtering of the drying agent, concentration of an organic layer under reduced pressure, and purification of residue using silica gel column chromatography (hexane/ethyl acetate=1/1 to 1/2) to obtain an objective compound (65 mg, 64.8%) as pale yellow solid.

$^1$H-NMR (200 MHzFT, TMS, CDCl$_3$) 1.30 (3H, t, J=7.1 Hz), 2.11 (1H, ddd, J=8.2, 9.5, 13.5 Hz), 2.56 (1H, dq, J=3.1, 13.5 Hz), 3.00-3.18 (2H, complex), 3.38-3.63 (2H, m), 4.21 (2H, q, J=7.1 Hz), 4.92 (1H, brt, J=7.2 Hz), 7.65 (1H, t, J=7.7 Hz), 7.75 (1H, brd, J=7.8 Hz), 8.09 (1H, s), 8.32 (1H, d, J=7.7 Hz), 8.37 (1H, brs) MS(ESI) m/z 367 [M+H]$^+$

Example 4

Synthesis of 5-hydroxy-3-(3-trifluoromethylphenyl)-5,6,7,8-tetrahydrocinnoline-7-carboxylic acid Ethyl 5-hydroxy-3-(3-trifluoromethylphenyl)-5,6,7,8-tetrahydrocinnoline-7-carboxylate (60 mg, 0.164 mmol) obtained in Example 3 was dissolved in dioxane (1 mL), followed by adding 0.1 ml of a concentrated HCl solution and stirring over night. The reaction liquid was concentrated, followed by neutralization with an aqueous solution of sodium hydrogen carbonate, making weak acid using a 1N aqueous solution of sodium hydrogen sulfate, extraction with ethyl acetate, drying with sodium sulfate anhydride, filtration, concentration of thus obtained organic layer under reduced pressure and purification of residue using silica gel column chromatography (methylene chloride/methanol=10/1) to obtain an objective compound (3 mg, 5.4%).

MS(ESI) m/z 339 [M+H]$^+$

Example 5

Synthesis of 5-oxo-3-(3-trifluoromethylphenyl)-7,8-dihydro-6H-cinnoline-7-carboxylic acid An objective compound (67.7 mg, 73.5%) was obtained by acid hydrolysis of ethyl 5-oxo-3-(3-trifluoromethylphenyl)-7,8-dihydro-6H-cinnoline-7-carboxylate (100 mg, 0.274 mmol) obtained in Example 2, similarly as in Example 4.

MS(ESI) m/z 337 [M+H]$^+$

Example 6

Synthesis of 7-methyl-3-(3-trifluoromethylphenyl)-5,6,7,8-tetrahydrocinnolin-5-ol An objective compound (917.9 mg, 90.9%) was obtained as white solid by processing of 5-oxo-3-(3-trifluoromethylphenyl)-7,8-dihydro-6H-cinnoline (1 g, 3.28 mmol) obtained in Example 66, similarly as in Example 3. Syn/anti ratio thereof was found to be about 9/1 by HPLC measurement.

$^1$H-NMR (200 MHzFT, TMS, CDCl$_3$) 1.22 (3H, d, J=6.6 Hz), 1.51 (1H, q, J=12.2 Hz), 1.88-2.44 (1H, m), 2.24-2.42 (1H, m), 2.73 (1H, ddd, J=1.1, 11.7, 18.0 Hz), 3.41 (1H, ddd, J=1.8, 5.2, 17.8 Hz), 4.90 (1H, q, J=5.8, 11.3 Hz), 7.62 (1H, t, J=7.7 Hz), 7.73 (1H, d, J=7.8 Hz), 8.14 (1H, d, J=1.1 Hz), 8.29 (1H, d, J=8.0 Hz), 8.34 (1H, s) MS(ESI) m/z 309 [M+H]$^+$

Example 7

Synthesis of 7-methyl-3-(3-trifluoro-methylphenyl)-5,6,7,8-tetrahydrocinnolin-5-ol To a benzene solution (16 mL) of 7-methyl-3-(3-trifluoromethylphenyl)-5,6,7,8-tetrahydrocinnolin-5-ol (92.5 mg, 0.3 mmol) obtained in Example 6 were added triphenylphosphine (480 mg, 1.47 mmol), 4-nitrobenzoic acid (221 mg, 1.32 mmol) and diethyl azodicarboxylate (0.23 mL, 1.47 mmol) and stirred at room temperature for 1 hour. The reaction liquid was purified as it is using silica gel column chromatography (hexane/ethyl acetate=2:1) to obtain anti-(±)-7-methyl-5-(4-nitrophenylcarbonyloxy)-3-(3-trifluoromethylphenyl)-5,6,7,8-tetrahydrocinnoline. Thus obtained compound was dissolved in methanol (5 ml), to which a 2N NaOH solution (1 ml) was added, followed by reaction at room temperature for 1 hour, adding distilled water (2 ml) and ethyl acetate (5 ml) for extraction and washing an organic layer obtained by the extraction with a saturated saline solution. After drying using sodium sulfate anhydride, the organic layer was concentrated under reduced pressure, followed by purification of residue using silica gel column chromatography (hexane/ethyl acetate=3/1) to obtain an objective compound (45 mg, 48.7%) as white solid. Syn/anti ratio thereof was found to be about 7/93 by HPLC measurement.

$^1$H-NMR (200 MHzFT, TMS, CDCl$_3$) 1.20 (3H, d, J=6.7 Hz), 1.78 (1H, ddd, J=4.5, 10.7, 14.0 Hz), 2.01-2.15 (1H, m), 2.20-2.45 (1H, m), 2.71 (1H, dd, J=10.1, 17.6 Hz), 3.41 (1H, ddd, J=1.3, 4.9, 17.6 Hz), 4.97 (1H, t, J=4.3 Hz), 7.63 (1H, t, J=7.7 Hz), 7.73 (1H, d, J=7.7 Hz), 7.92 (1H, s), 8.25-8.36 (2H, complex) MS(ESI) m/z 309 [M+H]$^+$

Example 8

Synthesis of syn-5-{N-(tert-butyloxycarbonyl)-L-prolyl}oxy-7-methyl-3-(3-trifluoromethylphenyl)-5,6,7,8-tetrahydrocinnoline To a tetrahydrofran solution (0.5 mL) of N-(tert-butyloxycarbonyl)-L-proline (21 mg, 0.098 mmol), 7-methyl-3-(3-trifluoromethylphenyl)-5,6,7,8-tetrahydrocinnolin-5-ol (23.4 mg, 0.076 mmol) and N,N-dimethylaminopyridine (catalytic amount) was added dicyclohexylcarbodiimide (24 mg, 0.114 mmol) and stirred at room temperature over night. The reaction liquid was added with hexane/ethyl acetate (1/1, 1 ml), followed by spreading on silica gel column with diameter of 10 mm and length of 15 mm, elution with ethyl acetate, concentration of the eluted liquid under reduced pressure and purification of residue using preparative thin-layer TLC (0.5 mm thickness, 20 cm×20 cm, 2 pieces, hexane/ethyl acetate=2/1) to obtain two kinds of diastereomers of objective compounds, as a low polarity component (17.4 mg) and a high polarity component (17.5 mg). A diastereomer mixture of 5.1 mg consisting of anti-substances was also obtained simultaneously.

MS(ESI) m/z 506 [M+H]$^+$

Example 9

Synthesis of syn-(−)-7-methyl-3-(3-trifluoromethylphenyl)-5,6,7,8-tetrahydrocinnolin-5-ol To a methanol solution (1 mL) of syn-diastereomer, as a low polarity component, obtained in Example 8 was added a 3N aqueous solution of NaOH (3 drops) and stirred at room temperature for 3.25 hours. The reaction liquid was concentrated under reduced pressure and thus obtained residue was spread on silica gel column with diameter of 10 mm and length of 15 mm, followed by elution with ethyl acetate and concentration of the eluted liquid under reduced pressure and purification of residue using preparative thin-layer TLC (0.5 mm thickness, 20 cm×10 cm, 2 pieces, hexane/ethyl acetate=1/1) to obtain an objective compound (10.1 mg).

MS (ESI) m/z 309 [M+H]$^+$ [α]$_D^{25}$ −131° (c0.51, methanol)

Example 10

Synthesis of syn-(+)-7-methyl-3-(3-trifluoromethylphenyl)-5,6,7,8-tetrahydrocinnolin-5-ol An objective compound (9.8 mg) was obtained by processing similarly as in Example 9, using a highly polar component, syn-diastereomer (17.5 mg), obtained in Example 8.

MS(ESI) m/z 309 [M+H]$^+$ [α]$_D^{25}$ +135° (c0.49, methanol)

Example 11

Synthesis of 5-acetyloxy-7-methyl-3-(3-trifluoromethylphenyl)-5,6,7,8-tetrahydrocinnoline To a pyridine solution (1 mL) of 7-methyl-3-(3-trifluoromethylphenyl)-5,6,7,8-tetrahydrocinnolin-5-ol (61.6 mg, 0.2 mmol) obtained in Example 6 was added acetic anhydride (0.027 mL, 0.24 mmol) under ice cooling and subjected to reaction at room temperature for 2 hours. The reaction solution was concentrated as it is under reduced pressure, followed by purification of thus obtained residue using silica gel column chromatography (hexane/ethyl acetate=3/1) to obtain an objective compound (57.6 mg, 82.3%).

$^1$H-NMR (200 MHzFT, TMS, CDCl$_3$) 1.23 (3H, d, J=6.6 Hz), 1.51 (1H, q, J=12.3 Hz), 2.07-2.27 (1H, m), 2.24 (3H, s), 2.32-2.46 (1H, m), 2.80 (1H, ddd, J=1.4, 11.5, 17.8 Hz), 3.44 (1H, ddd, J=1.8, 5.1, 17.9 Hz), 6.03 (1H, dd, J=6.1, 10.8 Hz), 7.65 (1H, t, J=7.7 Hz), 7.68 (1H, s), 7.75 (1H, d, J=7.6 Hz), 8.23 (1H, d, J=7.7 Hz), 8.33 (1H, brs) MS(ESI) m/z 351 [M+H]$^+$, 291 [M+H—CH$_3$COOH]$^+$ Example 12

Synthesis of 7-methyl-1-oxy-3-(3-trifluoromethylphenyl)-7,8-dihydro-6H-cinnolin-5-ol To a methylene chloride solution of 7-methyl-3-(3-trifluoromethylphenyl)-5,6,7,8-tetrahydrocinnolin-5-ol (90 mg, 0.294 mmol) obtained in Example 6 was added 3-chloroperbenzoic acid (122.5 mg, 0.71 mmol) under ice cooling and subjected to reaction for 2 hours. The solvent was concentrated, followed by adding a 3% aqueous solution of potassium carbonate (1 mL) and ethyl acetate (3 mL) for extraction, drying with sodium sulfate anhydride, removing the solvent under reduced pressure and purification of thus obtained residue using silica gel column chromatography (hexane/ethyl acetate=1/1 to 0/1) to obtain an objective compound (49.2 mg, 51.6%).
$^1$H-NMR (200 MHzFT, TMS, CDCl$_3$) 1.22 (3H, d, J=6.6 Hz), 1.51 (1H, dd, J=12.3 Hz), 1.66-2.20 (2H, complex), 2.21-2.36 (1H, m)2.40 (1H, dd, J=11.3, 19.3 Hz), 3.24 (1H, dd, J=5.3, 19.3 Hz), 4.88 (1H, dd, J=5.5, 11.4 Hz), 7.60 (1H, t, J=7.8 Hz), 7.69 (1H, d, J=7.7 Hz), 8.19 (1H, d, J=7.8 Hz), 8.25 (1H, brs) MS(ESI) m/z 325 [M+H]$^+$ Example 13

Synthesis of 5-oxo-1-oxy-3-(3-trifluoromethylphenyl)-7,8-dihydro-6H-cinnoline

An objective compound (124 mg, 38%) was obtained by processing 5-oxo-3-(3-trifluoromethylphenyl)-7,8-dihydro-6H-cinnoline (306 mg, 1 mmol) obtained in Example 66, similarly as in Example 12.
MS(ESI) m/z 323 [M+H]$^+$ Example 14

Synthesis of 7-hydroxymethyl-3-(3-trifluoromethylphenyl)-5,6,7,8-tetrahydrocinnolin-5-ol To a suspension of lithium aluminum hydride (14.5 mg, 0.38 mmol) in tetrahydrofran (1 mL) was added ethyl 5-oxo-3-(3-trifluoromethylphenyl)-7,8-dihydro-6H-cinnoline-7-carboxylate (92.8 mg, 0.25 mmol) obtained in Example 2 at −40° C., followed by stirring as it is for 1 hour and gradually elevating temperature up to room temperature. Ethyl acetate (3 mL) and a 1N HCl solution (0.5 mL) were added to quench the reaction, followed by further adding distilled water (2 mL) for extraction. An organic layer obtained by washing with a saturated saline solution was dried with sodium sulfate anhydride, followed by filtering the drying agent, concentrating the organic layer under reduced pressure and purification of thus obtained residue using silica gel column chromatography (methylene chloride/methanol=10/1) to obtain an objective compound (29.9 mg, 36.3%)
MS(ESI) m/z 325 [M+H]$^+$ .

Example 15

Synthesis of 3-(3-cyanophenyl)-7-methyl-7,8-dihydro-6H-cinnolin-5-one

An objective compound was obtained by processing similarly as in Reference Example 1, using 2-bromo-3'-cyanoacetophenone instead of 2-bromo-3'-trifluoromethylacetophenone, and 5-methyl-1,3-cyclohexanedione instead of 5-phenyl-1,3-cyclohexanedione, followed by processing thus obtained product similarly as in Reference Example 2 and Example 1.
MS(ESI) m/z 264 [M+H]$^+$ Example 16

Synthesis of 3-(3-cyanophenyl)-7-methyl-5,6,7,8-tetrahydrocinnolin-5-ol

An objective compound was obtained by processing 3-(3-cyanophenyl)-7-methyl-7,8-dihydro-6H-cinnolin-5-one obtained in Example 15, similarly as in Reference Example 3.
MS(ESI) m/z 266 [M+H]$^+$ Example 17

Synthesis of 7,7-dimethyl-3-(3-trifluoromethylphenyl)-5,6,7,8-tetrahydrocinnolin-5-ol An objective compound was obtained by processing similarly as in Reference Example 1, using 5,5-dimethyl-1,3-cyclohexanedione instead of 5-phenyl-1,3-cyclohexanedione, followed by processing thus obtained product, similarly as in Reference Example 2, Example 1 and Example 3.
MS(ESI) m/z 323 [M+H]$^+$ Example 18

Synthesis of 3-(3-trifluoromethylphenyl)-5,6,7,8-tetrahydrocinnolin-5-ol

An objective compound was obtained by processing similarly as in Reference Example 1 using 1,3-cyclohexanedione instead of 5-phenyl-1,3-cyclohexanedione, followed by processing thus obtained product similarly as in Reference Example 2, Example 1 and Example 3.
MS(ESI) m/z 295[M+H]$^+$ Example 19

Synthesis of 3-(3-bromophenyl)-7-methyl-7,8-dihydro-6H-cinnolin-5-one

An objective compound was obtained by processing similarly as in Reference Example 1 using 2,3'-dibromoacetophenone instead of 2-bromo-3'-trifluoromethylacetophenone and 5-methyl-1,3-cyclohexanedione instead of 5-phenyl-1,3-cyclohexanedione, followed by processing thus obtained product similarly as in Reference Example 2 and Example 1.
MS(ESI) m/z 317, 319 [M+H]$^+$

Example 20

Synthesis of 7-methyl-3-(3-nitrophenyl)-7,8-dihydro-6H-cinnolin-5-one

An objective compound was obtained by processing similarly as in Reference Example 1 using 2-bromo-3'-nitroacetophenone instead of 2-bromo-3'-trifluoromethylacetophenone, and 5-methyl-1,3-cyclohexanedione instead of 5-phenyl-1,3-cyclohexanedione, followed by processing thus obtained product similarly as in Reference Example 2 and Example 1.

MS(ESI) m/z 284 [M+H]$^+$

Example 21

Synthesis of 7-methyl-3-(3-tolyl)-7,8-dihydro-6H-cinnolin-5-one

An objective compound was obtained by processing similarly as in Reference Example 1 using 2-bromo-3'-methylacetophenone instead of 2-bromo-3'-trifluoromethylacetophenone, and 5-methyl-1,3-cyclohexanedione instead of 5-phenyl-1,3-cyclohexanedione, followed by processing thus obtained product similarly as in Reference Example 2 and Example 1.

MS(ESI) m/z 253 [M+H]$^+$

Example 22

Synthesis of 3-(3-methoxycarbonylphenyl)-7-methyl-7,8-dihydro-6H-cinnolin-5-one

An objective compound was obtained by processing similarly as in Reference Example 1 using methyl 3-(2'-bromoacetyl)benzoate instead of 2-bromo-3'-trifluoromethylacetophenone, and 5-methyl-1,3-cyclohexanedione instead of 5-phenyl-1,3-cyclohexanedione, followed by processing thus obtained product similarly as in Reference Example 2 and Example 1.

MS(ESI) m/z 297 [M+H]$^+$

Example 23

Synthesis of 3-(3-acetylaminophenyl)-7-methyl-7,8-dihydro-6H-cinnolin-5-one

An objective compound was obtained by processing similarly as in Reference Example 1 using 3-(2'-bromoacetyl)acetanilide instead of 2-bromo-3'-trifluoromethylacetophenone, and 5-methyl-1,3-cyclohexanedione instead of 5-phenyl-1,3-cyclohexanedione, followed by processing thus obtained product similarly as in Reference Example 2 and Example 1.

MS(ESI) m/z 296 [M+H]$^+$

Example 24

Synthesis of 3-(3-fluorophenyl)-7-methyl-7,8-dihydro-6H-cinnolin-5-one

An objective compound was obtained by processing similarly as in Reference Example 1 using 2-bromo-3'-fluoroacetophenone instead of 2-bromo-3'-trifluoromethylacetophenone, and 5-methyl-1,3-cyclohexanedione instead of 5-phenyl-1,3-cyclohexanedione, followed by processing thus obtained product similarly as in Reference Example 2 and Example 1.

MS(ESI) m/z 257 [M+H]$^+$

Example 25

Synthesis of 3-(3-methoxyphenyl)-7-methyl-7,8-dihydro-6H-cinnolin-5-one

An objective compound was obtained by processing similarly as in Reference Example 1 using 2-bromo-3'-methoxyacetophenone instead of 2-bromo-3'-trifluoromethylacetophenone, and 5-methyl-1,3-cyclohexanedione instead of 5-phenyl-1,3-cyclohexanedione, followed by processing thus obtained product similarly as in Reference Example 2 and Example 1.

$^1$H-NMR (200 MHzFT, TMS, CDCl$_3$) 1.27 (3H, d, J=6.2 Hz), 2.37-2.59 (2H, complex), 2.78-3.14 (2H, complex), 3.51-3.67 (1H, m), 3.92 (3H, s), 7.07 (1H, ddd, J=1.0, 2.6, 8.2 Hz), 7.45 (1H, t, J=8.0 Hz), 7.66 (1H, ddd, J=1.1, 1.5, 7.7 Hz), 7.78 (1H, dd, J=1.6, 2.6 Hz), 8.25 (1H, s) MS(ESI) m/z 269 [M+H]$^+$

Example 26

Synthesis of 7-benzyl-3-(3-trifluoromethylphenyl)-7,8-dihydro-6H-pyrido[3,4-c]-pyridazin-3-one An objective compound was obtained by processing similarly as in Reference Example 1 using 1-benzyl-5-hydroxy-1,6-dihydro-2H-pyridin-3-one instead of 5-phenyl-1,3-cyclohexanedione, followed by processing thus obtained product similarly as in Reference Example 2 and Example 1.

MS(ESI) m/z 384 [M+H]$^+$

Example 27

Synthesis of 7-(2-hydroxy-2-propyl)-3-(3-trifluoromethylphenyl)-5,6,7,8-tetrahydrocinnolin-5-ol A tetrahydrofran solution (1 mL) of ethyl 5-hyroxy-3-(3-trifluoromethylphenyl)-5,6,7,8-tetrahydrocinnoline-7-carboxylate (5 mg, 0.01 mmol) obtained in Example 3 was cooled to −20° C., followed by adding a tetrahydrofran solution (0.3 mL, 0.9 mmol) of 3N methylmagnesium bromide and stirring over night while elevating temperature. To the reaction liquid were added ethyl acetate (3 mL) and an acqueous solution of sodium hydrogen sulfate (1 mL), followed by fractionation, drying an organic layer thus obtained with sodium sulfate anhydride, filtering the drying agent and concentration of thus obtained organic layer under reduced pressure to obtain an objective compound (4.5 mg, 93.9%).

$^1$H-NMR (200 MHzFT, TMS, CDCl$_3$) 1.21 (3H, s), 1.24 (3H, s), 1.58-1.74 (1H, m), 1.94-2.14 (1H, m), 2.42-2.56 (1H, m), 3.03 (1H, dd, J=11.0, 17.6 Hz), 3.41 (1H, dd, J=5.2, 17.6 Hz), 4.88 (1H, dd, J=5.3, 10.4 Hz), 7.62 (1H, t, J=7.7 Hz), 7.73 (1H, d, J=7.7 Hz), 8.08 (1H, brs), 8.28 (1H, d, J=7.7 Hz), 8.34 (1H, brs) MS(ESI) m/z 353 [M+H]$^+$

Example 28

Synthesis of 3-((2-fluoro-5-trifluoromethyl)phenyl)-7-methyl-7,8-dihydro-6H-cinnolin-5-one An objective compound was obtained by processing similarly as in Reference Example 1 using 2-bromo-2'-fluoro-5'- trifluoromethylacetophenone instead of 2-bromo-3'-trifluoromethylacetophenone, and 5-methyl-1,3-cyclohexanedione instead of 5-phenyl-1,3-cyclohexanedione, followed by processing thus obtained product similarly as in Reference Example 2 and Example 1.
MS(ESI) m/z 325 [M+H]$^+$

Example 29

Synthesis of 3-((2-fluoro-5-trifluoromethyl)phenyl)-7-methyl-5,6,7,8-tetrahydrocinnolin-5-ol An objective compound was obtained by processing 3-((2-fluoro-5-trifluoromethyl)phenyl)-7-methyl-7,8-dihydro-6H-cinnolin-5-one obtained in Example 28 similarly as in Example 3.
MS(ESI) m/z 327 [M+H]$^+$

Example 30

Synthesis of 5,7-dimethyl-3-(3-trifluoromethylphenyl)-5,6,7,8-tetrahydro-cinnolin-5-ol 5-Oxo-3-(3-trifluoromethylphenyl)-7,8-dihydro-6H-cinnoline (200 mg, 0.65 mmol) obtained in Example 66 was dissolved in tetrahydrofuran (1 mL) and cooled to −20° C., followed by adding a tetrahydrofuran solution (0.26 mL, 0.78 mmol) of 3N methylmagnesium chloride to the reaction liquid and reacting for 3 hours while elevating temperature. To the reaction liquid was added distilled water (1 mL) to quench, followed by adding ethyl acetate (5 mL) and a 1N aqueous solution of sodium hydrogen sulfate (5 mL) for extraction, washing an organic layer with a saturated saline solution (3 ml), drying with sodium sulfate anhydride and purification of residue obtained by concentration using silica gel column chromatography (hexane/ethyl acetate=2/1 to 1/1) to obtain an objective compound (74.1 mg, 35%) as pale yellow crystal.
MS(ESI) m/z 323 [M+H]$^+$

Example 31

Synthesis of 5-(N-(tert-butoxycarbonyl)-L-alanyl)oxy-7-methyl-3-(3-trifluoromethylphenyl)-5,6,7,8-tetrahydrocinnoline 7-Methyl-3-(3-trifluoromethylphenyl)-5,6,7,8-tetrahydrocinnolin-5-ol (10 mg, 0.03 mmol) obtained in Example 6 was dissolved in a mixed solvent of tetrahydrofuran and dichloromethane (0.5 mL. 0.5 mL), followed by adding N-ethyl-N'-(3-dimethylaminopropyl)carbodiimide (9 mg, 0.045 mmol), N,N-dimethylaminopyridine (catalytic amount) and N-(tert-butoxycarbonyl)-L-alanine (9 mg, 0.045 mmol) and stirring at room temperature over night. After completion of the reaction, the reaction liquid was concentrated and thus obtained residue was purified using silica gel column chromatography (hexane/ethyl acetate=1/1) to obtain an objective compound.
MS(ESI) m/z 480 [M+H]$^+$

Example 32

Synthesis of 5-(L-alanyl)oxy-7-methyl-3-(3-trifluoromethylphenyl)-5,6,7,8-tetrahydrocinnoline dihydrochloride 5-(N-(tert-butoxycarbonyl)-L-alanyl)oxy-7-methyl-3-(3-trifluoromethylphenyl)-5,6,7,8-tetrahydrocinnoline obtained in Example 31 was dissolved in dioxane (0.5 mL, followed by adding a 4N HCl solution/dioxane (0.5 mL) under ice cooling and reacting over night. The reaction liquid was concentrated to dryness to obtain an objective compound as white solid.
MS(ESI) m/z 380 [M+H]$^+$

Example 33

Synthesis of 5-(N-(tert-butoxy-carbonyl)-β-(tert-butyl)-α-aspartyl)oxy-7-methyl-3-(3-tri-fluoromethylphenyl)-5,6,7,8-tetrahydrocinnoline An objective compound was obtained by processing similarly as in Example 31 using N-(tert-butoxycarbonyl)-β-(tert-butyl)-α-aspartic acid instead of N-(tert-butoxycarbonyl)-L-alanine.
MS(ESI) m/z 580 [M+H]$^+$

Example 34

Synthesis of 5-α-aspartyl)oxy-7-methyl-3-(3-trifluoromethylphenyl)-5,6,7,8-tetrahydrocinnoline dihydrochloride An objective compound was obtained as white solid by processing 5-(N-(tert-butoxycarbonyl)-β-(tert-butyl)-α-aspartyl)oxy-7-methyl-3-(3-trifluoromethylphenyl)-5,6,7,8-tetrahydrocinnoline obtained in Example 33 similarly as in Example 32.
MS(ESI) m/z 424 [M+H]$^+$

Example 35

Synthesis of 5-(N-(tert-butoxycarbonyl)-α-(tert-butyl)-β-aspartyl)oxy-7-methyl-3-(3-trifluoromethylphenyl)-5,6,7,8-tetrahydrocinnoline An objective compound was obtained as white solid by processing similarly as in Example 31, using N-(tert-butoxycarbonyl)-α-(tert-butyl)-β-aspartic acid instead of N-(tert-butoxycarbonyl)-L-alanine.
MS(ESI) m/z 580 [M+H]$^+$

Example 36

Synthesis of 5-(β-aspartyl)oxy-7-methyl-3-(3-trifluoromethylphenyl)-5,6,7,8-tetrahydrocinnoline dihydrochloride An objective compound was obtained as white solid by processing 5-(N-(tert-butoxycarbonyl)-β-(tert-butyl)-β-aspartyl)oxy-7-methyl-3-(3-trifluoromethylphenyl)-5,6,7,8-tetrahydrocinnoline obtained in Example 35 similarly as in Example 32.
MS(ESI) m/z 424 [M+H]$^+$

Example 37

Synthesis of 5-(N-(tert-butoxycarbonyl)-γ-(tert-butyl)-α-glutamyl)oxy-7-methyl-3-(3-tri-fluoromethylphenyl)-5,6,7,8-tetrahydrocinnoline An objective compound was obtained by processing similarly as in Example 31, using N-(tert-butoxycarbonyl)-γ-(tert-butyl)-α-glutamic acid instead of N-(tert-butoxycarbonyl)-L-alanine.
MS(ESI) m/z 594 [M+H]$^+$

Example 38

Synthesis of 5-(α-glutamyl)oxy-7-methyl-3-(3-trifluoromethylphenyl)-5,6,7,8-tetrahydrocinnoline dihydrochloride An objective compound was obtained as white solid by processing 5-(N-(tert-butoxycarbonyl)-γ-(tert-butyl)-α-glutamyl)oxy-7-methyl-3-(3-trifluoromethylphenyl)-5,6,7,8-tetrahydrocinnoline obtained in Example 37, similarly as in Example 32.

MS(ESI) m/z 438 [M+H]$^+$

Example 39

Synthesis of 5-(N-(tert-butoxycarbonyl)-α-(tert-butyl)-γ-glutamyl)oxy-7-methyl-3-(3-trifluoromethylphenyl)-5,6,7,8-tetrahydrocinnoline An objective compound was obtained by processing similarly as in Example 31, using N-(tert-butoxycarbonyl)-α-(tert-butyl)-γ-glutamic acid instead of N-(tert-butoxycarbonyl)-L-alanine.

MS (ESI) m/z 594 [M+H]$^+$

Example 40

Synthesis of 5-(γ-glutamyl)oxy-7-methyl-3-(3-trifluoromethylphenyl)-5,6,7,8-tetrahydrocinnoline dihydrochloride An objective compound was obtained as white solid by processing 5-(N-(tert-butoxycarbonyl)-α-(tert-butyl)-γ-glutamyl)oxy-7-methyl-3-(3-trifluoromethylphenyl)-5,6,7,8-tetrahydrocinnoline obtained in Example 39, similarly as in Example 32.

MS(ESI) m/z 438 [M+H]$^+$

Example 41

Synthesis of 5-(N-(tert-butoxycarbonyl)-glycyl)oxy-7-methyl-3-(3-trifluoromethylphenyl)-5,6,7,8-tetrahydrocinnoline An objective compound was obtained by processing similarly as in Example 31, using N-(tert-butoxycarbonyl)glycine instead of N-(tert-butoxycarbonyl)-L-alanine.

MS(ESI) m/z 466 [M+H]$^+$

Example 42

Synthesis of 5-glycyloxy-7-methyl-3-(3-trifluoromethylphenyl)-5,6,7,8-tetrahydrocinnoline dihydrochloride An objective compound was obtained by processing 5-(N-(tert-butoxycarbonyl)glycyl)oxy-7-methyl-3-(3-trifluoromethylphenyl)-5,6,7,8-tetrahydrocinnoline obtained in Example 41, similarly as in Example 32.

MS(ESI) m/z 366 [M+H]$^+$

Example 43

Synthesis of 5-(N-(tert-butoxycarbonyl)-L-leucyl)oxy-7-methyl-3-(3-trifluoromethylphenyl)-5,6,7,8-tetrahydrocinnoline An objective compound was obtained by processing similarly as in Example 31, using N-(tert-butoxycarbonyl)-L-leucine instead of N-(tert-butoxycarbonyl)-L-alanine.

MS(ESI) m/z 480 [M+H]$^+$

Example 44

Synthesis of 5-(L-leucyloxy)-7-methyl-3-(3-trifluoromethylphenyl)-5,6,7,8-tetrahydrocinnoline dihydrochloride An objective compound was obtained as white solid by processing 5-(N-(tert-butoxycarbonyl)-L-leucyl)oxy-7-methyl-3-(3-trifluoromethylphenyl)-5,6,7,8-tetrahydrocinnoline obtained in Example 43, similarly as in Example 32.

MS(ESI) m/z 380 [M+H]$^+$

Example 45

Synthesis of 5-(N(α),N(ε)-(di-tert-butoxycarbonyl)-L-lysyl)oxy-7-methyl-3-(3-trifluoromethylphenyl)-5,6,7,8-tetrahydrocinnoline An objective compound was obtained by processing similarly as in Example 31, using N(α),N(ε)-(di-tert-butoxycarbonyl)-L-lysine instead of N-(tert-butoxycarbonyl)-L-alanine.

MS(ESI) m/z 637 [M+H]$^+$

Example 46

Synthesis of 5-(L-lysyloxy)-7-methyl-3-(3-trifluoromethylphenyl)-5,6,7,8-tetrahydrocinnoline trihydrochloride An objective compound was obtained as white solid by processing 5-(N(α),N(ε)-(di-tert-butoxycarbonyl)-L-lysyl)oxy-7-methyl-3-(3-trifluoromethylphenyl)-5,6,7,8-tetrahydrocinnoline obtained in Example 45, similarly as in Example 32.

MS(ESI) m/z 437 [M+H]$^+$

Example 47

Synthesis of 5-(N-(tert-butoxycarbonyl)-L-methionyl)oxy-7-methyl-3-(3-trifluoromethyl-phenyl)-5,6,7,8-tetrahydrocinnoline An objective compound was obtained by processing similarly as in Example 31, using N-(tert-butoxycarbonyl)-L-methionine instead of N-(tert-butoxycarbonyl)-L-alanine.

MS (ESI) m/z 539 [M+H]$^+$

Example 48

Synthesis of 5-(L-methionyl)oxy-7-methyl-3-(3-trifluoromethylphenyl)-5,6,7,8-tetrahydrocinnoline dihydrochloride An objective compound was obtained as white solid by processing 5-(N-(tert-butoxycarbonyl)-L-methionyl)oxy-7- methyl-3-(3-trifluoromethylphenyl)-5,6,7,8-tetrahydrocinnoline obtained in Example 47, similarly as in Example 32.
MS(ESI) m/z 439 [M+H]$^+$ Example 49

Synthesis of 5-(N-(tert-butoxycarbonyl)-L-phenylalanyl)oxy-7-methyl-3-(3-trifluoromethylphenyl)-5,6,7,8-tetrahydrocinnoline An objective compound was obtained by processing similarly as in Example 31, using N-(tert-butoxycarbonyl)-L-phenylalanine instead of N-(tert-butoxycarbonyl)-L-alanine.
MS(ESI) m/z 556 [M+H]$^+$ Example 50

Synthesis of 5-(L-phenylalanyl)oxy-7-methyl-3-(3-trifluoromethylphenyl)-5,6,7,8-tetrahydrocinnoline dihydrochloride An objective compound was obtained as white solid by processing 5-(N-(tert-butoxycarbonyl)-L-phenylalanyl)oxy-7-methyl-3-(3-trifluoromethylphenyl)-5,6,7,8-tetrahydrocinnoline obtained in Example 49, similarly as in Example 32.
MS(ESI) m/z 456 [M+H]$^+$ Example 51

Synthesis of 5-(L-prolyl)oxy-7-methyl-3-(3-trifluoromethylphenyl)-5,6,7,8-tetrahydrocinnoline dihydrochloride An objective compound was obtained as white solid by processing syn-5-(N-(tert-butoxycarbonyl)-L-prolyl)oxy-7-methyl-3-(3-trifluoromethylphenyl)-5,6,7,8-tetrahydrocinnoline obtained in Example 8, as a highly polar component, similarly as in Example 32.
MS(ESI) m/z 406 [M+H]$^+$ Example 52

Synthesis of 5-(N-(tert-butoxycarbonyl)-L-valyl) oxy-7-methyl-3-(3-trifluoromethylphenyl)-5,6,7,8-tetrahydrocinnoline An objective compound was obtained by processing similarly as in Example 31, using N-(tert-butoxycarbonyl)-L-valine instead of N-(tert-butoxycarbonyl)-L-alanine.
MS (ESI) m/z 508. [M+H]$^+$ Example 53

Synthesis of 5-(L-valyloxy)-7-methyl-3-(3-trifluoromethylphenyl)-5,6,7,8-tetrahydrocinnoline dihydrochloride An objective compound was obtained as white solid by processing 5-(N-(tert-butoxycarbonyl)-L-valyl)oxy-7-methyl-3-(3-trifluoromethylphenyl)-5,6,7,8-tetrahydrocinnoline obtained in Example 52, similarly as in Example 32.
$^1$H-NMR (200 MHzFT, TMS, DMSO-d$_6$) 1.02 (3H, d, J=6.9 Hz), 1.07 (3H, d, J=6.9 Hz), 1.17 (3H, d, J=6.4 Hz), 1.54 (1H, q, J=11.6 Hz), 2.10-2.45 (3H, complex), 2.81 (1H, dd, J=11.1, 17.5 Hz), 2.37-2.59 (2H, complex), 2.78-3.14 (2H, complex), 3.51-3.67 (1H, m), 3.92 (3H, s), 6.11 (1H, dd, J=6.1, 10.1 Hz), 7.82 (1H, t, J=7.7 Hz), 7.92 (1H, d, J=7.9 Hz), 8.55 (1H, s), 8.63 (1H, d, J=7.7 Hz), 8.68 (1H, s), 8.85-9.03 (2H, br) [α]$_D$$^{25}$+105.2° (c1.016, MeOH) m.p. 201-3° C. MS(ESI) m/z 408 [M+H]$^+$ Example 54

Synthesis of (5S,7S)-5-(N-(tert-butoxycarbonyl)-D-phenylalanyl)oxy-7-methyl-3-(3-trifluoromethylphenyl)-5,6,7,8-tetrahydrocinnoline To a N,N-dimethylformamide solution (181 mL) of 7-methyl-3-(3-trifluoromethylphenyl)-5,6,7,8-tetrahydrocinnolin-5-ol (27.8 g, 90.4 mmol) obtained in Example 6 were added 1-[3-(dimethylamino)propyl]-3-ethylcarbodiimide hydrochloride (26 g, 135.7 mmol) and N-(tert-butoxycarbonyl)-D-phenylalanine (31.2 g, 117.6 mmol) with washing in N-methylpyrrolidone (36 ml), followed by adding N,N-dimethylaminopyridine (1.2 mg, 9.0 mmol) to the mixed liquid under ice cooling, stirring over night, adding ethyl acetate (0.6 mL) and distilled water (0.3 L) and washing thus extracted organic layer with a 5% by weight aqueous solution of potassium hydrogen sulfate (400 mL), a saturated aqueous solution of sodium bicarbonate (300 mL) and a 10% saline solution (300 mL) sequentially. To residue obtained after concentration of the organic layer was added ethanol (187 mL) and stirred over night at room temperature. Crystal generated was filtered and washed with ethanol (35 mL) to obtain the titled objective compound (14.8 g).
$^1$H-NMR (200 MHzFT, TMS, CDCl$_3$) 1.18 (3H, d, J=6.5 Hz), 1.22-1.38 (1H, m), 71 (9H, s), 1.90-2.23 (2H, complex), 2.72 (1H, dd, J=11.5, 17.9 Hz), 3.10 (2H, d, J=7.1 Hz), 3.40 (1H, ddd, J=1.4, 5.0, 17.7 Hz), 4.52 (1H, q, J=7.1 Hz), 5.02 (1H, d, J=6.5 Hz), 6.07 (1H, dd, J=5.9, 11.1 Hz), 7.01-7.40 (5H, complex), 7.60 (1H, t, J=7.8 Hz), 7.92 (1H, s), 8.32 (1H, d, J=7.7 Hz), 8.55 (1H, s) MS(ESI) m/z 556 [M+H]$^+$ Example 55

Synthesis of (5S,7S)-7-methyl-3-(3-trifluoromethylphenyl)-5,6,7,8-tetrahydrocinnolin-5-ol To a methanol solution (1.2 L) of (5S,7S)-5-(N-(tert-butoxycarbinyl)-D-phenylalanyl)oxy-7-methyl-3-(3-trifluoromethylphenyl)-5,6,7,8-tetrahydrocinnoline (280 g, 0.5 mol) obtained in Example 54 was added a 1N NaOH aqueous solution (0.6 L) at room temperature, followed by reaction at 40° C. over night. The reaction liquid was cooled to 10° C., followed by adding distilled water (1.8 L), stirring under suspension for 4 hours and filtering crystal to obtain the titled compound. Thus obtained compound was the same one obtained in Example 10.

Example 56

Synthesis of (5R,7R)-5-(N-(tert-butoxycarbonyl)-L-valyl)oxy-7-methyl-3-(3-trifluoromethyphenyl)-5,6,7,8-tetrahydrocinnoline An objective compound was obtained by processing similarly as in Example 54, using N-(tert-butoxycarbonyl)-L-valine instead of N-(tert-butoxycarbonyl)-L-phenylalanine.
$^1$H-NMR (200 MHzFT, TMS, CDCl$_3$) 1.03 (6H, dd, J=5.7, 6.8 Hz), 1.24 (3H, d, J=6.6 Hz), 1.48 (9H, s), 1.51-1.69 (1H, m), 2.04-2.37 (3H, complex), 2.79 (1H, dd, J=11.4, 17.9 Hz), 3.44 (1H, ddd, J=1.7, 4.9, 17.9 Hz), 4.15 (1H, dd, J=6.0, 7.9 Hz), 5.01 (1H, d, J=7.8 Hz), 6.18 (1H, dd, J=4.7 Hz), 7.61

(1H, t, J=7.8 Hz), 7.73 (1H, d), 8.00 (1H, s), 8.35 (1H, d, J=7.4 Hz), 8.56 (1H, s) MS (ESI) m/z 508 [M+H]$^+$

Example 57

Synthesis of (5R,7R)-7-methyl-3-(3-trifluoromethylphenyl)-5,6,7,8-tetrahydrocinnolin-5-ol The titled objective compound was obtained by processing (5R,7R)-5-(N-(tert-butoxycarbonyl)-L-valyl)oxy-7-methyl-3-(3-trifluoromethylphenyl)-5,6,7,8-tetrahydrocinnoline obtained in Example 56, similarly as in Example 55. Thus obtained compound was the same one obtained in Example 9.

Example 58

Synthesis of (−)-(5R,7R)-5-(L-valyl)oxy-7-methyl-3-(3-trifluoromethylphenyl)-5,6,7,8-tetrahydrocinnoline dihydrochloride The titled objective compound was obtained as white solid by processing (5R,7R)-5-(N-(tert-butoxycarbonyl)-L-valyl)oxy-7-methyl-3-(3-trifluoromethylphenyl)-5,6,7,8-tetrahydrocinnoline obtained in Example 56, similarly as in Example 32.

$^1$H-NMR (200 MHzFT, TMS, DMSO-d$_6$) 0.87-1.22 (10H, complex), 1.60 (1H, q, J=12.0 Hz), 2.12-2.40 (3H, complex), 2.81 (1H, dd, J=11.4, 17.6 Hz), 3.30 (1H, dd, J=4.3, 17.6 Hz), 4.04 (1H, t, J=4.8 Hz), 6.22 (1H, dd, J=5.9, 10.6 Hz), 7.81 (1H, t, J=7.8 Hz), 7.92 (1H, d, J=8.0 Hz), 8.46-8.70 (2H, complex), 8.82-9.04 (2H, br) [α]$_D^{25}$−68.8° (c0.999, MeOH) m.p. 162-5° C. MS (FAB) m/z 408 [M+H]$^+$

Example 59

Synthesis of (5S,7R)-5-(N-(tert-butoxycarbonyl)-L-valyl)oxy-7-methyl-3-(3-trifluoromethylphenyl)-5,6,7,8-tetrahydrocinnoline The titled compound was obtained by Mitsunobu reaction using N-(tert-butoxycarbonyl)-L-valine instead of 4-nitrobenzoic acid, and (5R,7R)-7-methyl-3-(3-trifluoromethylphenyl)-5,6,7,8-tetrahydrocinnolin-5-ol of 7-methyl-3-(3-trifluoromethylphenyl)-5,6,7,8-tetrahydrocinnolin-5-ol, in Example 7.

MS(ESI) m/z 508 [M+H]$^+$

Example 60

Synthesis of (5S,7R)-7-methyl-3-(3-trifluoromethylphenyl)-5,6,7,8-tetrahydrocinnolin-5-ol The titled objective compound was obtained by processing (5S,7R)-5-(N-(tert-butoxycarbonyl)-L-valyl)oxy-7-methyl-3-(3-trifluoromethylphenyl)-5,6,7,8-tetrahydrocinnoline obtained in Example 59, similarly as in Example 55.

Example 61

Synthesis of (+)-(5S,7R)-5-(L-valyl)oxy-7-methyl-3-(3-trifluoromethylphenyl)-5,6,7,8-tetrahydrocinnoline dihydrochloride The titled objective compound was obtained by processing (5S,7R)-5-(N-(tert-butoxycarbonyl)-L-valyl)oxy-7-methyl-3-(3-trifluoromethylphenyl)-5,6,7,8-tetrahydrocinnoline obtained in Example 59, similarly as in Example 32.

$^1$H-NMR (200 MHzFT, TMS,DMSO-d$_6$) 0.92 (3H, d, J=3.7 Hz), 0.96 (3H, d, J=3.7 Hz), 1.13 (3H, d, J=6.6 Hz), 1.72-1.92 (1H, m), 2.02-2.36 (3H, complex), 2.72 (1H, dd, J=11.4, 17.6 Hz), 3.36 (1H, dd, J=4.3, 17.6 Hz), 3.79 (1H, brt, J=4.5 Hz), 6.12 (1H, brs), 7.82 (1H, t, J=7.6 Hz), 7.92 (1H, d, J=8.0 Hz), 7.98-8.50 (1H, br), 8.52 (1H, d, J=8.5 Hz), 8.60 (1H, s), 8.70-8.88 (2H, br) [α]$_D^{25}$+36.9° (c0.975,MeOH) m.p. 186-9° C. MS(FAB) m/z 408 [M+H]$^+$

Example 62

Synthesis of (5R,7S)-5-(N-(tert-butoxycarbonyl)-L-valyl)oxy-7-methyl-3-(3-trifluoromethylphenyl)-5,6,7,8-tetrahydrocinnoline The titled compound was obtained by Mitsunobu reaction using N-(tert-butoxycarbonyl)-L-valine instead of 4-nitrobenzoic acid, and (5S,7S)-7-methyl-3-(3-trifluoromethylphenyl)-5,6,7,8-tetrahydrocinnolin-5-ol instead of 7-methyl-3-(3-trifluoromethylphenyl)-5,6,7,8-tetrahydrocinnolin-5-ol, in Example 7.

MS(ESI) m/z 508 [M+H]$^+$

Example 63

Synthesis of (5R,7S)-7-methyl-3-(3-trifluoromethylphenyl)-5,6,7,8-tetrahydrocinnolin-5-ol The titled objective compound was obtained by processing (5R,7S)-5-(N-(tert-butoxycarbonyl)-L-valyl)oxy-7-methyl-3-(3-trifluoromethylphenyl)-5,6,7,8-tetrahydrocinnoline obtained in Example 62, similarly as in Example 55.

Example 64

Synthesis of (−)-(5R,7S)-5-(L-valyl)oxy-7-methyl-3-(3-trifluoromethylphenyl)-5,6,7,8-tetrahydrocinnoline dihydrochloride The titled objective compound was obtained by processing (5R,7S)-5-(N-(tert-butoxycarbonyl)-L-valyl)oxy-7-methyl-3-(3-trifluoromethylphenyl)-5,6,7,8-tetrahydrocinnoline obtained in Example 62, similarly as in Example 32.

$^1$H-NMR (200 MHzFT, TMS, DMSO-d$_6$) 0.95-1.06 (6H, complex), 1.15 (3H, d, J=6.6 Hz), 1.77-2.34 (4H, complex), 2.74 (1H, dd, J=10.9, 17.4 Hz), 3.37 (1H, dd, J=4.2, 17.5 Hz), 3.75-3.90 (1H, m), 6.20 (1H, brt, J=3.3 Hz), 7.82 (1H, t, J=7.7 Hz), 7.93 (1H, t, J=7.7 Hz), 8.50-8.59 (2H, complex), 8.70-8.88 (3H, complex) [α]$_D^{25}$−15.8° (c1.010, MeOH) m.p. 181-5° C. MS(FAB) m/z 408 [M+H]$^+$

Reference Example 1

Synthesis of 3-hydroxy-2-[2-oxo-2-(3-trifluoromethylphenyl)ethyl]-5-phenylcyclohex-2-enone To a chloroform solution (2 mL) of 2-bromo-3'-trifluoromethylacetophenone (534.1 mg, 2 mmol) and 5-phenyl-1,3-cyclohexanedione (376.5 mg, 2 mmol) was added potassium carbonate (276.4 mg, 2 mmol) and stirred under suspension at room temperature over night. The reaction liquid was added with ethyl acetate (5 mL), to filter off undissolved substance, followed by concentration of thus obtained organic layer under reduced pressure and purification of concentrated residue using silica gel column chromatography (hexane/ethyl acetate=1/1) to obtain a crude product, which was further purified by suspension (hexane 1 ml/ethyl acetate about 0.2 ml) to obtain an objective compound (257.8 mg, 35.0%).
MS(ESI) m/z 375 [M+H]+

Reference Example 2

Synthesis of 7-phenyl-3-(3-trifluoromethylphenyl)-4,6,7,8-tetrahydro-1H-cinnoline-5-one To an ethanol solution (1 mL) of 3-hydroxy-2-[2-oxo-2-(3-trifluoromethylphenyl)-ethyl]-5-phenylcyclohex-2-enone (257.8 mg, 0.69 mmol) obtained in Reference Example 1 were added hydrazine hydrochloride (72.3 mg, 0.69 mmol) and triethylamine (0.19 mL, 1.38 mmol) and stirred at room temperature for 1 hour. The reaction liquid was added with distilled water (3 mL) and filtered off yellow crystal generated to obtain an objective crude product (603 mg).
MS(ESI) m/z 375 [M+H]+

Reference Example 3

Synthesis of ethyl 3-hydroxy-5-oxo-cyclohexa-3-ene carboxylate

To an ethanol solution (200 mL) of 3,5-dihydroxybenzoic acid (25 g, 162.2 mmol) was added sulfuric acid (3 mL) and stirred over night at room temperature and then under heating at 65° C. for 4 days. The reaction liquid was concentrated under reduced pressure and poured into ice water (about 300 mL) while stirring to filter off white crystal, 3,5-dihydroxy-benzoic acid ethyl ester (22.8 g, 77.2%).

3,5-Dihydroxybenzoic acid ethyl ester (10 g, 54.89 mmol) was dissolved in ethanol (15 mL), followed by adding sodium formate (4.48 g, 65.87 mmol), replacing inside a reactor with nitrogen at 30° C. for 15 minutes, adding palladium on carbon (364 mg) and reacting at 30° C. for 3 hours then at 40° C. over night. Catalyst was filtered off, followed by neutralization with a 1N HCl solution, concentration under reduced pressure and purification of thus obtained residue with silica gel column chromatography (hexane/ethyl acetate=1/1 to 0/1) to obtain an objective compound (1.53 g, 15.1%).
$^1$H-NMR (200 MHzFT, TMS, CDCl$_3$) 1.26 (3H, dt, J=1.8, 7.1 Hz), 2.66 (2H, d, J=2.7 Hz), 2.83 (1H, dd, J=1.8, 6.6 Hz), 3.01-3.19 (1H, m), 3.32-3.55 (1H, m), 4.18 (2H, q, J=7.2 Hz), 5.51 (1H, s), 5.80-6.10 (1H, br) MS(ESI) m/z 185 [M+H]+

Reference Example 4

Synthesis of 5-hydroxy-1-methyl-1,6-dihydro-2H-pyridine-3-one

To an ethanol solution (30 mL) of N-methylglycine ethyl ester hydrochloride (3.06 g, 20 mmol) were added sodium hydrogen carbonate (3.36 g, 40 mmol) and bromoacetone (1.68 mL, 20 mmol) and stirred over night at 60° C. The reaction liquid was filtered, followed by concentration under reduced pressure and adding to residue thus obtained a 10% HCl solution (250 mL) and ethyl acetate (250 mL) for fractionation. To thus obtained water layer was added sodium hydrogen carbonate till pH>7, followed by extraction with ethyl acetate, drying with magnesium sulfate anhydride and concentration under reduced pressure to obtain an objective compound, ethyl N-methyl-N-(2-oxopropyl)-glycinate (2.58 g, 74%). Thus obtained compound was dissolved in tert-butanol (40 mL), followed by adding potassium tert-butoxide (1.67 g, 14.9 mmol) and stirring at room temperature for 30 minutes. The reacting liquid was concentrated under reduced pressure and residue thus obtained was purified with silica gel column chromatography (chloroform/methanol/30% ammonia water=6/2.5/0.5) to obtain an objective compound (1.83 g, 96%).
MS(ESI) m/z 128 [M+H]+

Reference Example 5

Synthesis of 1-benzyl-5-hydroxy-1,6-dihydro-2H-pyridine-3-one

An objective compound was obtained by processing similarly as in Reference Example 4, using ethyl N-methylglycinate hydrochloride instead of ethyl N-benzylglycinate hydrochloride.
MS(ESI) m/z 204 [M+H]+

Example 65

Synthesis of 7-methyl-3-(3-trifluoromethylphenyl)-4,6,7,8-tetrahydro-1H-cinnolin-5-one To an ethanol solution (14 mL) of 3-hydroxy-5-methyl-2-[2-oxo-2-(3-trifluoromethylphenyl)-ethyl]-cyclohex-2-enone (438.7 mg, 1.4 mmol) obtained in Reference Example 7 were added hydrazine hydrochloride (177 mg, 1.7 mmol) and triethylamine (0.49 mL, 35 mmol) and stirred at room temperature for 3 hours. The reaction liquid was concentrated, followed by purification of residue with silica gel column chromatography (methylene chloride/methanol=30/1) to obtain an objective compound (100.9 mg, 23.3%).
$^1$H-NMR (200 MHzFT, TMS, CDCl$_3$) 1.13 (3H, d, J=5.9 Hz), 2.00-2.60 (5H, complex), 3.27 (1H, d, J=9.3 Hz), 3.57 (1H, d, J=9.3 Hz), 7.49 (1H, brs), 7.54 (1H, brd, J=7.9 Hz), 7.65 (1H, brd, J=7.7 Hz), 7.94 (1H, brd, J=7.8 Hz), 8.08 (1H, brs) MS(ESI) m/z 309 [M+H]+

Example 66

Synthesis of 7-methyl-3-(3-trifluoromethylphenyl)-7,8-dihydro-6H-cinnolin-5-one

To a pyridine solution (1 mL) of 7-methyl-3-(3-trifluoromethylphenyl)-4,6,7,8-tetrahydro-1H-cinnolin-5-one (136.2 mg, 0.44 mmol) obtained in Example 65 was added p-toluenesulfonic acid hydrate (84 mg, 0.44 mmol) and stirred at room temperature for 3 days. The reaction liquid was concentrated, followed by purification of residue obtained with silica gel column chromatography (methylene chloride/methanol=30/1) to obtain an objective compound (89.0 mg, 66.1%).
$^1$H-NMR (200 MHzFT, TMS, CDCl$_3$) 1.28 (3H, d, J=1.3 Hz), 2.40-2.62 (2H, complex), 2.80-2.89 (1H, m), 2.90-3.19 (1H, m), 3.55-3.70 (1H, m), 7.68 (1H, brt, J=7.7 Hz), 7.74 (1H, brd, J=7.7 Hz), 8.29 (1H, s), 8.34 (1H, brd, J=7.3 Hz), 8.44 (1H, brs) MS(ESI) m/z 307 [M+H]+

Example 67

Synthesis of [7-methyl-3-(3-trifluoromethylphenyl)-7,8-dihydro-6H-cinnolin-5-ylidene]-hydrazine To an ethanol solution (3 mL) of 7-methyl-3-(3-trifluoromethylphenyl)-4,6,7,8-terahydro-1H-cinnolin-5-one (230 mg, 0.74 mmol) obtained in Example 65 were added hydrazine hydrochloride (77.3 mg, 0.74 mmol) and triethylamine (0.206 mL, 1.48 mmol) and stirred at room temperature over night. The reaction liquid was concentrated, followed by purification of residue with silica gel column chromatography (hexane/ethyl acetate=1/1) to obtain an objective compound (29.5 mg, 12.5%).

$^1$H-NMR (200 MHzFT, TMS, CDCl$_3$) 1.26 (3H, d, J=1.3 Hz), 2.03 (1H, dd, J=10.6, 16.4 Hz), 2.06-2.36 (1H, m), 2.75 (1H, ddd, J=1.6, 4.4, 16.4 Hz), 2.83 (1H, dd, J=10.8, 16.5 Hz), 3.49 (1H, ddd, J=1.5, 3.6, 16.5 Hz), 4.5-6.5 (2H, m), 7.65 (1H, t, J=7.7 Hz), 7.75 (1H, d, J=7.8 Hz), 8.26-8.47 (3H, complex) MS(ESI) m/z 321 [M+H]$^+$ Example 68

Synthesis of 3-(3-trifluoromethylphenyl)-7,8-dihydro-6H-cinnolin-5-one

An objective compound was obtained by reaction using 1,3-cyclohexanedione instead of 5-methyl-1,3-cyclohexanedione used in Reference Example 7, followed by processing thus obtained product similarly as in Example 65 and then Example 66.

MS(ESI) m/z 293 [M+H]$^+$

Example 69

Synthesis of 7,7-dimethyl-3-(3-trifluoromethylphenyl)-7,8-dihydro-6H-cinnolin-5-one An objective compound was obtained by reaction using 5,5-dimethyl-1,3-cyclohexanedione instead of 5-methyl-1,3-cyclohexanedione used in Reference Example 7, followed by processing thus obtained product similarly as in Example 65 and then Example 66.

MS(ESI) m/z 321 [M+H]$^+$

Reference Example 6

Synthesis of 2-bromo-3'-trifluoromethylacetophenone

To a toluene solution (423 mL) of commercially available 3'-trifluoromethylacetophenone (79.6 g, 0.423 mol) was added pyridinium bromide perbromide (135.4 g, 0.423 mol) under ice cooling and stirred for 5 hours while heating up to room temperature. The reaction liquid was ice cooled again, followed by dropwise adding 400 mL of distilled water to stop reaction and fractionation. A toluene layer was washed with 400 mL of a saturated aqueous solution of sodium bicarbonate, followed by drying with magnesium sulfate anhydride and concentration under reduced pressure and distillation under reduced pressure to obtain an objective compound (92.35 g, 81.7%).

$^1$H-NMR (200 MHzFT, TMS, CDCl$_3$) 4.46 (2H, s), 7.66 (1H, brt, J=7.9 Hz), 7.88 (1H, brd, J=7.6 Hz), 8.19 (1H, brd, J=7.5 Hz), 8.25 (1H, brs) b.p. 92° C./3 mmHg Reference Example 7

Synthesis of 3-hydroxy-5-methyl-2-[2-oxo-2-(3-trifluoromethylphenyl)-ethyl]-cyclohex-2-enone To a chloroform solution (240 mL) of 2-bromo-3'-trifluoromethylacetophenone (63.5 g, 0.238 mol) obtained in Reference Example 6 and 5-methyl-1,3-cyclohexanedione (30 g, 0.238 mol) was added potassium carbonate (32.9 g, 0.238 mol) and stirred at room temperature over night. The reaction liquid was filtered and white solid obtained, which was suspended in distilled water (300 mL), followed by dropwise adding a concentrated HCl solution (300 mL) under ice cooling, extracting with ethyl acetate (700 mL) and ethanol (50 mL), drying with sodium sulfate anhydride, concentration of thus obtained organic layer under reduced pressure, adding ethyl acetate (200 mL) to residue obtained, stirring in suspension at room temperature for 4 hours and filtering off crystal to obtain an objective compound (25.7 mg, 34.6%).

$^1$H-NMR (200 MHzFT, TMS, CDCl$_3$) 1.06 (3H, d, J=5.9 Hz), 1.98-2.63 (5H, complex), 3.77 (1H, d, J=13.6 Hz), 4.29 (1H, d, J=13.6 Hz), 7.63 (1H, brt, J=7.6 Hz), 7.87 (1H, brd, J=7.8 Hz), 8.43-8.52 (2H, complex), 9.64 (1H, s) MS(ESI) m/z 313 [M+H]$^+$ Example 70

Synthesis of 7-methyl-3-(3-trifluoromethylphenyl)cinnolin-5-ol

To an ethyl acetate solution (1 mL) of 7-methyl-3-(3-trifluoromethylphenyl)-7,8-dihydro-6H-cinnolin-5-one (306 mg, 1.0 mmol) obtained in Example 66 was added cupric bromide (446 mg, 2.0 mmol), followed by reaction under heating and refluxing for 8 hours, adding saturated sodium bicarbonate aqueous solution (2 mL) to the reaction liquid and extraction with ethyl acetate. To residue obtained after concentration of an organic layer under reduced pressure was added ethyl acetate (1 mL) and filtered off solid obtained to get an objective product (17 mg, 5.5%) as yellow solid.

$^1$H-NMR (200 MHzFT, TMS,DMSO-d$_6$) 2.54 (3H, s), 7.02 (1H, s), 7.79 (1H, s), 7.80-7.95 (2H, complex), 8.52-8.69 (2H, complex), 11.1(1H, s) MS(ESI) m/z 305 [M+H]$^+$ Example 71

Synthesis of 5-methoxy-7-methyl-3-(3-trifluoromethylphenyl)cinnoline

To an acetone solution (5 mL) of 7-methyl-3-(3-trifluoromethylphenyl)cinnolin-5-ol (30.4 mg, 0.1 mmol) obtained in Example 70 were added methyl iodide (0.006 mL, 0.11 mmol) and potassium carbonate (13.8 mg, 0.11 mmol), followed by reaction at room temperature over night. To residue obtained by concentration of the reaction liquid under reduced pressure was added distilled water (1 mL) and extracted with ethyl acetate. Residue obtained after concentration of an organic layer under reduced pressure was purified with silica gel column chromatography (hexane/ethyl acetate=1/1) to obtain an objective compound (5 mg, 15%) as white solid.

MS(ESI) m/z 319 [M+H]$^+$

Example 72

Synthesis of 5-acetyloxy-7-methyl-3-(3-trifluoromethylphenyl)cinnoline

To a pyridine solution (2 mL) of 7-methyl-3-(3-trifluoromethylphenyl)cinnolin-5-ol (60 mg, 0.2 mmol) obtained in Example 70 was added acetic anhydride (3 mL), followed by reaction at room temperature over night. The reaction liquid was concentrated under reduced pressure, followed by adding distilled water (1 mL), extraction with ethyl acetate and purification of residue obtained after concentration of an organic layer under reduced pressure, with HPLC column chromatography (hexane/ethyl acetate=3/1) to obtain an objective compound (25 mg, 36%) as pale yellow solid.

MS (ESI) m/z 347 [M+H]$^+$

Example 73

Synthesis of 5-benzyloxy-7-methyl-3-(3-trifluoromethylphenyl)cinnoline

To an acetone solution (5 mL) of 7-methyl-3-(3-trifluoromethylphenyl)cinnolin-5-ol (69 mg, 0.2 mmol) obtained in Example 70 were added benzyl bromide (0.024 mL) and potassium carbonate (28 mg, 0.2 mmol), followed by stirring at room temperature over night and refluxing under heating for 3 hours. The reaction liquid was further added with benzyl bromide (0.024 mL) and potassium carbonate (28 mg, 0.2 mmol), followed by stirring at room temperature over night, concentration of the reaction liquid under reduced pressure, adding distilled water (1 mL), extraction with ethyl acetate and purification of residue obtained after concentration of an organic layer under reduced pressure, with HPLC column chromatography (hexane/ethyl acetate=3/1) to obtain an objective compound (8 mg, 10%).

MS(ESI) m/z 395 [M+H]$^+$

Test Example 1

Antitumor Effect in vitro Using Mammary Tumor Cell MCF-7 and MDA-MB-453

Each MCF-7, 2000 cells, and MDA-MB-453, 4000 cells, was inoculated using 10% serum added RPMI 1640 medium (Asahi Technoclass Inc.) into a 96 well plate. After incubating these cells at 37° C., under atmosphere of 5% $CO_2$/95% air for 24 hours, each of the compounds of Examples 1, 2, 6, 9-13, 20, 24, 26, 27, 65, 66, 70, 71, 72 and 73 was added and incubated for further 3 days. Cells were stained with a 0.05% methylene blue solution and measured using a microplate reader (Benchmark Plus, Bio-Rad Laboratories) by absorption at 660 nm. Proliferation inhibition rate was calculated by the following equation, and 50% cell proliferation inhibitory concentrations of the compounds of Examples 1, 2, 6, 9-13, 20, 24, 26, 27, 65, 66, 70, 71, 72 and 73 were shown in Table 2.

Proliferation inhibition rate=(1−absorbance with drug addition÷absorbance in control)×100

TABLE 2

| | $IC_{50}$ (μg/ml) | |
|---|---|---|
| | MCF-7 | MDA-MB-453 |
| Compound of Example 1 | 0.0388 | 0.0395 |
| Compound of Example 2 | 1.9600 | 1.5700 |
| Compound of Example 6 | 0.0499 | 1.4700 |
| Compound of Example 9 | 0.0772 | 0.3390 |
| Compound of Example 10 | 0.0982 | 1.5400 |
| Compound of Example 11 | 0.0455 | 0.8480 |
| Compound of Example 13 | 0.0671 | 0.9510 |
| Compound of Example 20 | 1.4060 | 9.3500 |
| Compound of Example 24 | 3.5700 | 4.9500 |
| Compound of Example 26 | 0.3610 | 8.9300 |
| Compound of Example 27 | 0.2710 | 4.7200 |
| Compound of Example 65 | 0.10 | 1.64 |
| Compound of Example 66 | 0.05 | 1.26 |
| Compound of Example 70 | 0.181 | 0.551 |
| Compound of Example 71 | 0.158 | 3.360 |
| Compound of Example 72 | 0.138 | 0.420 |
| Compound of Example 73 | 0.399 | 2.600 |

As obvious from Table 1, the compounds of Examples 1, 2, 6, 9-13, 20, 24, 26, 27, 65, 66, 70, 71, 72 and 73 have antitumor effect to inhibit proliferation of mammary tumor cells.

Further, a test was conducted by using 4000 mammary tumor cells, T-47D, by adding a compound of example 65 or 66 under the same condition hereinabove. $IC_{50}$ value was 0.67 μg/ml and 0.28 μg/ml, respectively, and the compound also exhibited antitumor effect against mammary tumor cell T-47D.

Test Example 2

Antitumor Effect in vivo Using Mammary Tumor Cell ZR-75-1

Mammary tumor cells ZR-75-1 were inoculated in dorsal subcutaneous region of female nude mice. The compound of example 66 and example 53 was administered orally at dose level of 500 mg/kg, once a day, for 14 days consecutively from the point of initiating logarithmic growth of tumor cells. Conjugate axis and transverse axis of tumor were measured in the time dependent manner, and tumor volume was calculated by the following equation. Relative tumor volume, wherein tumor volume at the time of initiating administration was set as 1, was calculated. Effectiveness was judged by value (T/C) wherein tumor volume in the treated group is divided by tumor volume in the control group.

tumor volume=conjugate axis×conjugate axis×transverse axis/2

T/C values on day 15 after initiating administration of the compounds of Example 66 and example 53 are 30.3% and 34.0%, respectively. Consequently, the compounds of Example 66 and example 53 were also shown to have antitumor effect which inhibited proliferation of mammary tumor in vivo.

INDUSTRIAL APPLICABILITY

According to the present invention, a cinnoline analogue or a physiologically acceptable salt thereof, which can be used effectively for prevention or treatment of tumor, and an antitumor agent and a cell proliferation inhibitor comprising a cinnoline analogue or a physiologically acceptable salt thereof, as an active ingredient, are provided.

We claim:

1. A 3-phenyl-cinnoline compound represented by the general formula (1):

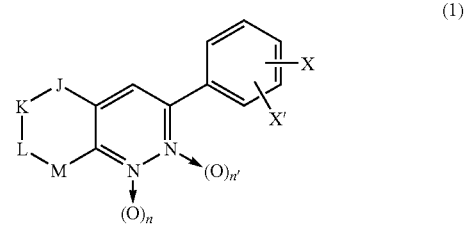

wherein J is A-C—B (C is a carbon atom); A is an O—Y group (O is an oxygen atom; Y is a hydrogen atom, a lower alkyl group having 1 to 6 carbon atoms which may be substituted by a phenyl group or a lower acyl group having 1 to 6 carbon atoms); B is a hydrogen atom, a lower alkyl group having 1 to 6 carbon atoms, or a carbonyl group together with A or =N—NH$_2$ together with A; K is CH$_2$; L is W—C—H (C is a carbon atom); W is a lower alkyl group having 1 to 6 carbon atoms which may have a substituent selected from a group consisting of a hydroxyl group, a lower alkoxyl group having 1 to 6 carbon atoms and a phenyl group, a phenyl group, a carboxyl group, a lower alkoxycarbonyl group having 2 to 7 carbon atoms or a hydrogen atom; M is $CH_2$, or J-K-L-M is C(O—Y)=CH—C(W)=CH (Y and W have the same meanings hereinabove); X is a halogenated lower alkyl group having 1 to 6 carbon atoms, a nitro group, a cyano group, or a halogen atom; X' is a halogen atom or a hydrogen atom; and n and n' each independently is 0 or 1, or a physiologically acceptable salt thereof.

* * * * *